(12) United States Patent
Nordström et al.

(10) Patent No.: US 8,859,501 B2
(45) Date of Patent: *Oct. 14, 2014

(54) PROTOFIBRIL-BINDING ANTIBODIES AND THEIR USE IN THEREAPEUTIC AND DIAGNOSTIC METHODS FOR PARKINSON'S DISEASE, DEMENTIA WITH LEWY BODIES AND OTHER ALPHA-SYNUCLEINOPATHIES

(71) Applicant: BioArctic Neuroscience AB, Stockholm (SE)

(72) Inventors: Eva Nordström, Rönninge (SE); Alex Kasrayan, Stockholm (SE); Monica Ekberg, Stockholm (SE); Valentina Screpanti Sundquist, Spånga (SE); Lars Lannfelt, Stockholm (SE); Mats Holmquist, Sollentuna (SE)

(73) Assignee: BioArctic Neuroscience AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/957,239

(22) Filed: Aug. 1, 2013

(65) Prior Publication Data
US 2013/0309251 A1 Nov. 21, 2013

Related U.S. Application Data

(63) Continuation of application No. 13/578,710, filed as application No. PCT/IB2011/050826 on Feb. 25, 2011.

(60) Provisional application No. 61/406,260, filed on Oct. 25, 2010, provisional application No. 61/308,638, filed on Feb. 26, 2010.

(51) Int. Cl.
*A61K 39/00* (2006.01)
*C07K 16/18* (2006.01)
*G01N 33/68* (2006.01)

(52) U.S. Cl.
CPC ............. *C07K 16/18* (2013.01); *C07K 2317/33* (2013.01); *G01N 2800/2814* (2013.01); *G01N 2800/2821* (2013.01); *G01N 2800/302* (2013.01); *C07K 2317/34* (2013.01); *G01N 2800/30* (2013.01); *G01N 33/6896* (2013.01); *G01N 2800/2835* (2013.01); *G01N 2800/387* (2013.01)
USPC ..................................... 514/17.7; 424/139.1

(58) Field of Classification Search
None
See application file for complete search history.

(56) References Cited

U.S. PATENT DOCUMENTS

| 7,179,463 B2 | 2/2007 | Lannfelt et al. |
| 7,700,719 B2 | 4/2010 | Lannfelt et al. |

(Continued)

FOREIGN PATENT DOCUMENTS

| WO | 00/02053 A2 | 1/2000 |
| WO | 02/03911 A2 | 1/2002 |

(Continued)

OTHER PUBLICATIONS

Kobayash et al. 2004 "Study of association between alpha-synuclein gene polymorphism and methamphetamine psychosis/dependence" Ann N Y Acad Sci 1025:325-34 (abstract only).*

(Continued)

*Primary Examiner* — Gregory S Emch
*Assistant Examiner* — Adam M Weidner
(74) *Attorney, Agent, or Firm* — Porter Wright Morris & Arthur LLP

(57) ABSTRACT

Antibodies and fragments thereof have high affinity for human α-synuclein protofibrils and low binding of α-synuclein monomers, wherein the antibodies or fragments have specified Complementarity Determining Region (CDR) sequences. Compositions comprise such an antibody or fragment and methods of detecting α-synuclein protofibrils use such an antibody or fragment. In further embodiments, methods of preventing, delaying onset of or treating a neurodegenerative disorder with α-synuclein pathology comprise administering such an antibody or fragment, and such an antibody or fragment is used in the manufacture of a pharmaceutical composition for treatment of a neurodegenerative disorder with α-synuclein pathology. Such an antibody or fragment is used in the diagnosis or monitoring of the development of a neurodegenerative disorder with α-synuclein pathology, and in methods for reducing or inhibiting α-synuclein aggregation by administration of such an antibody or fragment.

55 Claims, 10 Drawing Sheets

(56) References Cited

U.S. PATENT DOCUMENTS

| | | |
|---|---|---|
| 7,919,088 B2 | 4/2011 | Schenk et al. |
| 7,977,316 B2 | 7/2011 | Schenk et al. |
| 8,147,833 B2 | 4/2012 | Schenk et al. |
| 8,506,959 B2 | 8/2013 | Schenk et al. |
| 2002/0162129 A1 | 10/2002 | Lannfelt et al. |
| 2005/0203010 A1 | 9/2005 | Kim |
| 2006/0018918 A1 | 1/2006 | Chang |
| 2006/0058233 A1 | 3/2006 | Schenk et al. |
| 2006/0259986 A1 | 11/2006 | Chilcote et al. |
| 2007/0248606 A1 | 10/2007 | Lannfelt et al. |
| 2008/0014194 A1 | 1/2008 | Schenk et al. |
| 2008/0181902 A1 | 7/2008 | Lannfelt et al. |
| 2009/0155246 A1 | 6/2009 | Gellerfors et al. |
| 2009/0258009 A1 | 10/2009 | Gellerfors et al. |
| 2011/0052498 A1 | 3/2011 | Lannfelt et al. |
| 2012/0076726 A1 | 3/2012 | Gellerfors et al. |
| 2012/0100129 A1 | 4/2012 | Gellerfors et al. |
| 2012/0230912 A1 | 9/2012 | Gellerfors et al. |

FOREIGN PATENT DOCUMENTS

| | | |
|---|---|---|
| WO | 2004/041067 A2 | 5/2004 |
| WO | 2005/047860 A2 | 5/2005 |
| WO | 2006/020581 A2 | 2/2006 |
| WO | 2006/045037 A2 | 4/2006 |
| WO | 2007/089862 A2 | 8/2007 |
| WO | 2009/133521 A2 | 11/2009 |

OTHER PUBLICATIONS

Noori-Daloii et al. 2010 "Alpha- and beta-synucleins mRNA expression in lymphocytes of schizophrenia patients" Genet Test Mol Biomarkers 14(5):725-9 (abstract only).*

Nuber et al. 2008 "Neurodegeneration and motor dysfunction in a conditional model of Parkinson's disease" Neuro Dis 28(10):2471-2484.*

Rafii and Aisen 2009 "Recent developments in Alzheimer's disease therapeutics" BMC Medicine 7:7.*

Emadi et al, Journal of Molecular Biology, 368(4):1132-1144 (2007).

Papachroni et al, Journal of Neurochemistry, 101(3):749-756 (2007).

Masliah et al, Neuron, 46(6):857-868 (2005).

Crews et al, Neurotoxicity Research, 16(3): 306-317 (Oct. 1, 2009).

Emadi et al, Biochemistry, 43(10):2871-2878 (2004).

Nasstrom et al, Biochemical and Biophysical Research Communications, 378(4):872-876 (Jan. 23, 2009).

Qin et al, Journal of Biological Chemistry, 282(8):5862-5870 (2007).

Rudikoff et al, Proceedings of the National Academy of Sciences, 79:1979-1983 (1982).

Wahlberg et al, Alzheimer's & Dementia: The Journal of the Alzheimer's Association, 4(4):T481-482 (Jul. 1, 2008).

Kostka et al, The Journal of Biological Chemistry, 283(16):10992-11003 (Apr. 18, 2008).

Nannenga et al, FEBS Letters, 582(4):517-522 (Jan. 28, 2008).

Lynch et al, Journal of Molecular Biology, 377(1):136-147 (2007).

Miller et al, Molecular Therapy, 12(3):394-401 (2005).

McGuire-Zeiss et al, Biochemical and Biophysical Research Communications, 349(4):1198-1205 (2006).

McGuire-Zeiss et al, Molecular Therapy: The Journal of the American Society of Gene Therapy, 9(Supp. 1):S86 (2004).

Zhou et al, Molecular Therapy, Academic Press, 10(6):1023-1031 (2004).

Pountney et al, Neurotoxicity Research, 7(1-2):59-67 (2005).

Trostchansky et al, The Biochemical Journal, 393(Pt 1):343-349 (2006).

Lee et al, Journal of Neurochemistry, 76(4):998-1009 (2001).

Davidson et al, The Journal of Biological Chemistry, 273(16):9443-9449 (1998).

Shtilerman et al, Biochemistry, 41(12):3855-3860 (2002).

Beyer et al, Current Medicinal Chemistry, 15(26):2748-2759 (Nov. 2008).

Nasstrom et al, Alzheimer's & Dementia: The Journal of the Alzheimer's Association, 4(4):T754 (Jul. 1, 2008).

Bergstrom et al, Alzheimer's & Dementia: The Journal of the Alzheimer's Association, 4(4):T435 (Jul. 1, 2008).

Conway et al, Proceedings of the National Academy of Science USA, 97:571-576 (2000).

Sharon et al, Neuron, 37:583-595 (2003).

Tokuda et al, Neurology, 75:1766-1772 (2010).

Freichel et al, Neurobiol. Aging, 28:1421-1435 (2007).

Masliah, Neuron, 46:857-868, (2005).

* cited by examiner

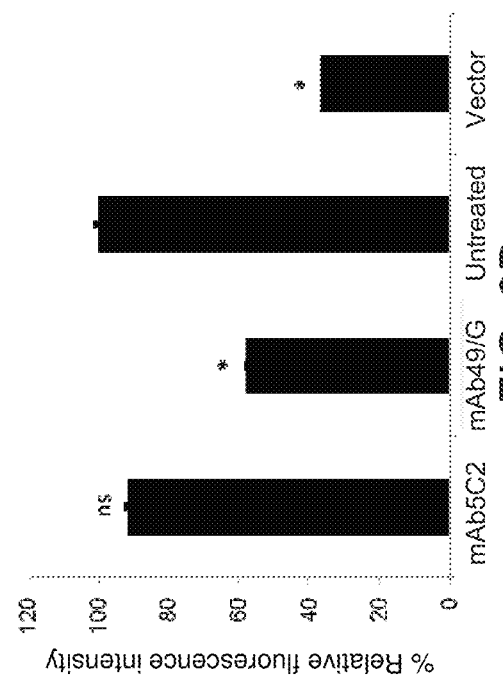
FIG. 9A
FIG. 9B

PROTOFIBRIL-BINDING ANTIBODIES AND THEIR USE IN THEREAPEUTIC AND DIAGNOSTIC METHODS FOR PARKINSON'S DISEASE, DEMENTIA WITH LEWY BODIES AND OTHER ALPHA-SYNUCLEINOPATHIES

FIELD OF THE INVENTION

The present invention is directed to antibodies or fragments thereof having high affinity for human α-synuclein protofibrils and low binding of α-synuclein monomers, wherein the antibodies or fragments have specified Complementarity Determining Region (CDR) sequences. The present invention is also directed to compositions comprising such an antibody or fragment and to methods of detecting α-synuclein protofibrils using such an antibody or fragment. In further embodiments, the invention is directed to methods of preventing, delaying onset of or treating a neurodegenerative disorder with α-synuclein pathology by administering such an antibody or fragment, and to use of such an antibody or fragment in the manufacture of a pharmaceutical composition for treatment of a neurodegenerative disorder with α-synuclein pathology. The invention is also directed to use of such an antibody or fragment in the diagnosis or monitoring of the development of a neurodegenerative disorder with α-synuclein pathology, and to methods for reducing or inhibiting α-synuclein aggregation by administration of such an antibody or fragment.

BACKGROUND OF THE INVENTION

Parkinson's disease (PD) and dementia with Lewy bodies (DLB) are the two most prevalent examples of neurodegenerative disorders with α-synuclein brain pathology. PD is the most common movement disorder and is characterized by rigidity, hypokinesia, tremor and postural instability. PD is believed to affect approximately four to six million people worldwide. DLB represents 5-15% of all dementia. In addition to forgetfulness and other dementing symptoms that often fluctuate, DLB patients typically suffer from recurrent falls and visual hallucinations.

Intraneuronal accumulation of α-synuclein either results in the formation of Lewy bodies, round eosinophilic hyaline 10-20 μm large inclusions, or Lewy neurites, elongated thread-like dystrophic axons and dendrites. In the PD brain, deposition of Lewy bodies and Lewy neurites are mostly limited to neurons connecting striatum with substantia nigra. These cells are crucial for the execution of movement and postural functions, explaining the nature of PD symptoms. In the DLB brain, widespread depositions of Lewy bodies and Lewy neurites are found both in midbrain and cortical areas.

Alpha-synuclein is a protein which is mainly found intraneuronally. Within the neuron, α-synuclein is predominantly located presynaptically and it has therefore been speculated that it plays a role in the regulation of synaptic activity. Three main isoforms of α-synuclein have been identified, of which the longest and most common form comprises 140 amino acids. This isoform has been used and alpha-synuclein (α-synuclein) related characteristics of antibodies according to the invention refer to this isoform of α-synuclein.

In addition to α-synuclein, Lewy bodies consist of a wide range of molecules, one of which is 4-hydroxy-2-nonenal (HNE), an α,β-unsaturated hydroxyalkenal (Qin et al., 2007). It has been shown in vitro that HNE can modify α-synuclein and thereby facilitate α-synuclein oligomerization. In particular, HNE has been shown to increase and stabilize the formation of protofibrils, i.e. soluble larger oligomeric forms of α-synuclein (Qin et al., 2007; WO 2009/133521, incorporated herein by reference).

Oxidative stress has been implicated in a number of neurodegenerative disorders characterized by the pathological accumulation of misfolded α-synuclein. Various reactive oxygen species can induce peroxidation of lipids such as cellular membranes or lipoproteins and also result in the generation of highly reactive aldehydes from poly-unsaturated fatty acids (Yoritaka et al., 1996).

Brain pathology indicative of Alzheimer's disease (AD), i.e. amyloid plaques and neurofibrillary tangles, are seen in approximately 50% of cases with DLB. It is unclear whether the existence of parallel pathologies implies two different diseases or just represents a variant of each respective disorder. Sometimes the cases with co-pathology are described as having a Lewy body variant of AD (Hansen et al., 1990).

Recent research has implicated a role of α-synuclein in AD and Down's syndrome, as the α-synuclein protein has been demonstrated to accumulate in the limbic region in these disorders (Crews et al., 2009).

HNE reacts and modifies side chains of cysteine, histidine and lysine, substantially altering the structure and physical properties of these side chains. Hence, HNE can either react with the C-3 carbon or with the aldehyde group or by combinations thereof. Hence, HNE can covalently modify proteins, either inter- or intramolecularly.

Genetics of Parkinson's Disease and Dementia with Lewy Bodies

Rare dominantly inherited forms of PD and DLB can be caused by point mutations or duplications of the α-synuclein gene. The pathogenic mutations A30P and A53T (Kruger et al., 1998) (Polymeropoulos et al., 1998) and duplication of the gene (Chartier-Harlin et al. 2004) have been described to cause familial PD, whereas one other α-synuclein mutation, E46K (Zarranz et al., 2004) as well as triplication of the α-synuclein gene (Singleton et al., 2003) have been reported to cause either PD or DLB.

The pathogenic consequences of the α-synuclein mutations are only partly understood. However, in vitro data have shown that the A30P and A53T mutations increase the rate of aggregation (Conway et al., 2000). A broad range of differently composed α-synuclein species (monomers, dimers, oligomers, including protofibrils) are involved in the aggregation process, all of which may have different toxic properties. It is not clear which molecular species exert toxic effects in the brain. However, recent research suggests that oligomeric forms of α-synuclein are particularly neurotoxic. Additional evidence for the role of oligomers is given by the observation that certain α-synuclein mutations (A30P and A53T) causing hereditary Parkinson's disease, lead to an increased rate of oligomerization.

It is not completely known how the α-synuclein aggregation cascade begins. Possibly, an altered conformation of monomeric α-synuclein initiates formation of dimers and trimers, which continue to form higher soluble oligomers, including protofibrils, before these intermediately sized species are deposited as insoluble fibrils in Lewy bodies. It is also conceivable that the α-synuclein oligomers, once they are formed, can bind new monomers and/or smaller multimers of α-synuclein and hence accelerate the fibril formation process. Such seeding effects can possibly also occur in the extracellular space as recent evidence suggests that α-synuclein pathology may propagate from neuron to neuron in the diseased brain.

Apart from the neuropathological changes in α-synucleinopathies, levels of α-synuclein protein are generally increased in affected brain regions (Klucken et al., 2006).

The major pathology in α-synucleinopathies is intracellular, which poses a challenge to the immune therapeutic approach. However, it is likely that a fraction of actively induced or passively administrated antibodies can bind their target antigens also intraneuronally. Moreover, the identification of α-synuclein in both plasma and cerebrospinal fluid (El-Agnaf et al., 2006) illustrates that the protein is not exclusively found within neurons. Reducing such extracellular α-synuclein may shift the equilibrium between the intracellular and extracellular protein pools and result also in decreased intracellular α-synuclein. Evidence suggests that α-synuclein in solution can penetrate lipid bilayers in cellular membranes and thereby become internalized or exported out of the cell. Recent findings demonstrate that α-synuclein exerts toxic effects in the extracellular space, thus providing a plausible explanation for how α-synuclein pathology spreads throughout the brain as the disease progresses. Studies showed that Lewy pathology was transmitted to grafted neurons in transplanted PD patients (Li et al. 2008). Furthermore, α-synuclein is transmitted via endocytocis to neighboring neurons, and cell-to-cell transmission of α-synuclein aggregates has been linked to neuronal cell death and pathological progression in PD and other α-synucleinopathies (Desplats et al. 2009).

Diagnosis of PD and DLB

There is a need for improved diagnostic tools and methods to identify a risk for a neurodegenerative disease with α-synuclein pathology. Today, no biochemical method can aid the clinician to diagnose the patient clinical symptoms in the early stages of the disease, before substantial damage to the brain has already occurred.

The importance of accurate diagnostic assays will become even greater as new therapeutic possibilities emerge. As of today, only symptomatic treatment (by substituting the loss of active dopamine in the brain) is available for PD patients. For DLB, even less therapeutic options are available. Nevertheless, clinicians are frequently evaluating possible beneficial effects on DLB patients with the standard treatment for AD, i.e. cholinesterase inhibitors. In either way, none of the existing treatment strategies for α-synucleinopathies are directed against the underlying disease processes. In addition, there is also a need for monitoring the disease progression and the treatment effect. For a review on different approaches aimed at altering the progression of Parkinson's disease, see George et al. 2009.

In view of the above-mentioned involvement of α-synuclein in several neurodegenerative disorders, there is a need for novel treatments that can eliminate or reduce the effect of toxic α-synuclein species, as well as a need for good biomarkers to monitor new interventions and provide good prognostic specificity.

SUMMARY OF THE INVENTION

The present invention is directed to improved antibodies and fragments thereof having high affinity for human α-synuclein protofibrils and low binding of α-synuclein monomers. The present invention is also directed to compositions comprising such an antibody or fragment and to methods of detecting α-synuclein protofibrils using such an antibody or fragment. In further embodiments, the invention is directed to methods of preventing, delaying onset of or treating a neurodegenerative disorder with α-synuclein pathology by administering such an antibody or fragment, and to use of such an antibody or fragment in manufacture of a pharmaceutical composition for treatment of a neurodegenerative disorder with α-synuclein pathology. The invention is also directed to use of such an antibody or fragment in the diagnosis or monitoring of the development of a neurodegenerative disorder with α-synuclein pathology, and to methods for reducing or inhibiting α-synuclein aggregation by administration of such an antibody or fragment.

In one embodiment, the antibody or fragment thereof has high affinity for human α-synuclein protofibrils and low binding of α-synuclein monomers, and has three variable heavy (VH) CDR sequences (VH-CDR-1, VH-CDR-2, and VH-CDR-3) and three variable light (VL) CDR sequences (VL-CDR-1, VL-CDR-2, and VL-CDR-3), wherein the six CDR sequences of the antibody or fragment thereof are selected from the following respective groups:
VH-CDR-1 SEQ ID NOS: 22, 23, 24, 25, 26 or 27
VH-CDR-2 SEQ ID NOS: 28, 29, 30, 31, 32, 33 or 34
VH-CDR-3 SEQ ID NOS: 35, 36, 37, 38, 39 or 40
VL-CDR-1 SEQ ID NOS: 41, 42, 43, 44, 45 or 46
VL-CDR-2 SEQ ID NOS: 47, 48 or 49
VL-CDR-3 SEQ ID NOS: 50, 51, 52, 53, 54 or 55.

In another embodiment, the antibody or fragment thereof has high affinity for human α-synuclein protofibrils and low binding of α-synuclein monomers, and has three variable heavy (VH) CDR sequences (VH-CDR-1, VH-CDR-2, and VH-CDR-3) and three variable light (VL) CDR sequences (VL-CDR-1, VL-CDR-2, and VL-CDR-3), wherein the six CDR sequences of the antibody or fragment thereof are selected from the following respective groups, and sequences having greater than 70, 80, 90, 95 or 98% similarity with any of said sequences of the respective groups:
VH-CDR-1 SEQ ID NOS: 22, 23, 24, 25, 26 or 27
VH-CDR-2 SEQ ID NOS: 28, 29, 30, 31, 32, 33 or 34
VH-CDR-3 SEQ ID NOS: 35, 36, 37, 38, 39 or 40
VL-CDR-1 SEQ ID NOS: 41, 42, 43, 44, 45 or 46
VL-CDR-2 SEQ ID NOS: 47, 48 or 49
VL-CDR-3 SEQ ID NOS: 50, 51, 52, 53, 54 or 55,
and wherein the antibody or fragment thereof binds to an epitope within the amino acid region 113-140, e.g. 113-131, and in particular the epitopes 125-131, 121-124, 121-127, 121-131, 113-123 or 136-140, of immobilized linear α-synuclein in a model system comprising 15-mer alpha-synuclein peptides with 11 amino acids overlap.

The antibodies, fragments, compositions and methods according to the invention provide improvements in the diagnosis, monitoring, prevention, delay of onset and/or treatment of neurodegenerative disorders with α-synuclein pathology in individuals having and/or at risk of developing such disorders.

Additional aspects, embodiments and advantages of the various embodiments of the present invention will be more apparent in view of the detailed description.

BRIEF DESCRIPTION OF THE DRAWING

The detailed description will be more fully understood in view of the Drawings, in which:

FIG. 2A shows protofibril specific monoclonal antibody mAb49/G binds with high affinity to human α-synuclein protofibrils stabilized by either HNE or ONE. FIG. 2B shows the monoclonal antibody also binds with high affinity to HNE-stabilized protofibrils of human mutated forms of α-synuclein, A30P and A53T.

FIG. 4A shows a schematic of the protofibril specific antibody mAb49/G used as both the capturing antibody and the detection antibody. FIG. 4B shows the standard curve generated with HNE-stabilized α-synuclein protofibrils. Assay performance reached a limit of quantification LOQ=9 pM.

FIG. 7A shows 38E2/7 binding of Lewy bodies and neurites in PD substantia nigra and a positive α-α-synuclein control. FIG. 7B shows 38E2/7 binding of Lewy bodies and neurites in DLB cortex and substantia nigra and a positive α-α-synuclein control. FIG. 7C shows various antibodies binding Lewy bodies and neurites in DLB cortex and substantia nigra and a negative control. FIG. 7D shows various antibodies binding Lewy bodies and neurites in PD substantia nigra and a negative control. FIG. 7E shows no binding of 38E2/7 in non-disease related substantia nigra and a positive α-α-synuclein control. FIG. 7F shows a comparison of 38E2/7 binding and a positive α-Aβ control in cortex of an Alzheimer's disease patient.

FIGS. 9A and 9B show fluorescence data measured using an Axiovert200 microscope equipped with a FITC epifluorescence filter as described in Example 10. FIG. 9A shows treated cells while FIG. 9B shows data calculated as relative % decrease in fluorescence intensity compared to antibody untreated alpha-synuclein over expressing cells, which was set to 100%.

Figure 1:
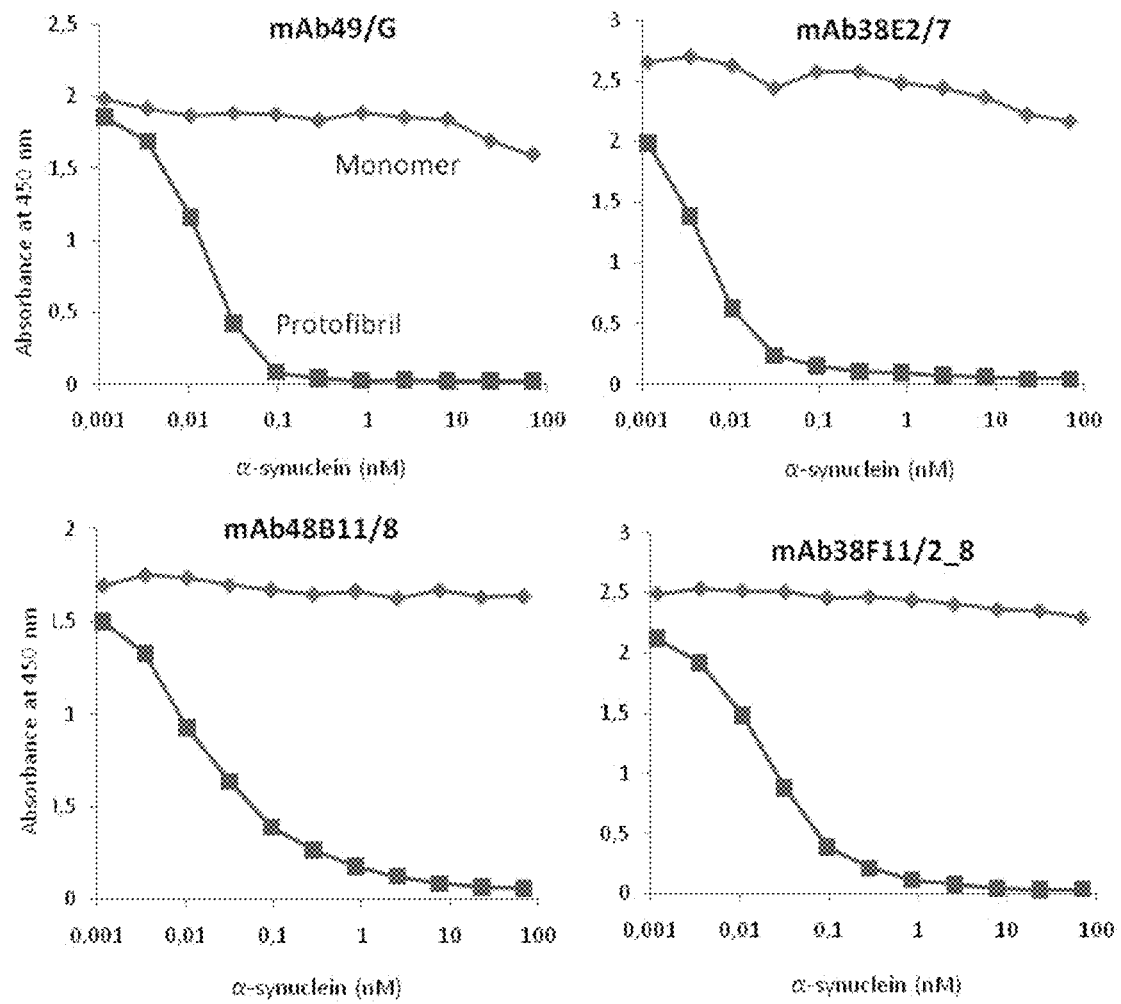
FIG. 1 shows the performance of protofibril specific monoclonal antibodies as determined by a competition ELISA. The assay was performed with HNE-stabilized α-synuclein protofibrils as described in Example 4.

The various figures will be more fully understood in view of the Examples set forth below.

DETAILED DESCRIPTION

In a first embodiment, the present invention is directed to improved antibodies and fragments thereof having high affinity for human α-synuclein protofibrils and low binding of α-synuclein monomers. In a specific embodiment, the antibodies are of class IgG or mutations thereof. Within the present disclosure, the high affinity for human α-synuclein protofibrils means that the antibodies or fragments exhibit a dissociation constant $K_d$ less than $10^{-7}$ M for human α-synuclein protofibrils. As is known in the art, protofibrils are soluble oligomers of α-synuclein. Typical protofibrils have a molecular weight in a range of from about 1000 to about 5000 kDa, suitably measured using size exclusion chromatography with globular proteins used as references, but the invention is not limited to such typical protofibrils. In addition, within the present disclosure, the low binding of α-synuclein monomers means that the binding of an antibody or fragment according to the invention to α-synuclein monomers is at least 100 times less than that to α-synuclein protofibrils. In a specific embodiment, these binding affinities are measured according to competition ELISA, for example, as described in Example 4.

The invention further relates to methods and uses of such antibodies and fragments for improvements in preventing, delaying onset of, treating, monitoring and/or diagnosing of neurodegenerative disorders with α-synuclein pathology, including, but not limited to, Parkinson's disease (PD), dementia with Lewy bodies (DLB), the Lewy body variant of Alzheimer's disease, multiple system atrophy, psychosis, schizophrenia, and Creutzfeldt-Jakob disease. In α-synucleinopathies, aggregated α-synuclein as Lewy bodies and Lewy neurites accumulate in the brain and, in some indications, also in other organs.

Examples of antibodies according to the invention have been developed by classical hybridoma techniques. The antibodies may be polyclonal or monoclonal. In a specific embodiment, the antibodies are monoclonal. While the present disclosure refers in many instances to antibodies and fragments thereof, for purposes of convenience, the term "antibody" in the present disclosure includes fragments thereof, meaning active fragments thereof, i.e. fragments having the same characteristics that are used for definition of an antibody according to the invention, namely high affinity for α-synuclein oligomers/protofibrils and low binding of α-synuclein monomers. The antibodies and fragments thereof exhibit high efficiency in clearance of pathogenic forms of α-synuclein.

The invented antibodies bind aggregated forms, in particular protofibrils, comprising α-synuclein that is either unmodified or conjugated, for example, conjugated to 4-hydroxy-2-nonenal (HNE) or 4-oxo-2-nonenal (ONE), or other α,β-unsaturated hydroxyalkenals, or poly-unsaturated fatty acids, that stabilize a pathogenic protofibril/oligomeric α-synuclein epitope. Said epitope or epitopes are present on conformationally altered or modified α-synuclein, i.e. α-synuclein protofibrils and oligomers which are present in human brain from patients with α-synucleinopathies, such as, but not limited to, Parkinson's disease, DLB, etc. The invented antibodies also bind the pathogenic protofibril/oligomeric structures formed by α-synuclein mutants, e.g. A30P and A53T (Kruger et al., 1998) (Polymeropoulos et al., 1997) that have been described to cause familial PD. Another example of such targets for antibodies of the invention are protofibrils formed by the mutant α-synuclein E46K, causing PD or DLB.

In one specific embodiment of the invention, monoclonal antibodies are provided for differentiating, diagnosing, identifying risk for developing, and/or treating α-synucleinopathology related disorders, including, but not limited to, e.g. Parkinson's disease, dementia with Lewy bodies, Lewy body variant of Alzheimer's disease, Alzheimer's disease, Down's syndrome, multiple system atrophy, psychosis, schizophrenia, Creutzfeldt-Jakob disease and other neurodegenerative disorders.

The antibodies and fragments of the invention comprise defined amino acid sequences of the CDR1-3 regions on the variable light (VL) and variable heavy (VH) chains from antibodies having high affinity for soluble α-synuclein protofibrils containing the "PD and or DLB disease epitope." In specific embodiments, the CDR regions are combined with modifications of the Fc region to modulate effector functions such as, but not limited to, Fc receptor binding, complement factor C1q binding, effecting half-life, complement activation and inflammation processes. The constant region of an antibody has many important functions notably binding Fc-receptors and complement factor C1q. The latter function can be inactivated to avoid inflammatory reactions.

The inventive antibodies and fragments having high affinity for α-synuclein protofibrils and low binding to α-synuclein monomers have the following distinct advantages as compared to other known immunotherapeutic treatment modalities:

1) The inventive antibodies and fragments target and inactivate or at least reduce disease causing α-synuclein protofibrils, e.g. by inhibition of oligomerization (see Example 10) or by other mechanisms.
2) The high affinity for α-synuclein protofibrils exhibited by the inventive antibodies and fragments reduces the clinical dose needed for an effective treatment.
3) The inventive antibodies and fragments provide a modality for accurate dosing in elderly patients compared to an active immunization strategy, such as vaccine.
4) The low binding to α-synuclein monomers in the periphery/systemically thus allow more antibodies/fragments to be available for binding and elimination of α-synuclein oligomeric forms in the brain.
5) The antibodies and fragments reduce the risk for inflammatory side-effects, e.g. meningioencephalitis, by low or no binding to complement factor C1q.

One aspect of the invention is the discovery of the antibody amino acid sequences of the CDR regions that play an important role for binding of human wild type and mutant α-synuclein protofibrils. Antibodies having binding sites (CDR regions) according to the invention are characterized by high affinity for wild-type human α-synuclein oligomers/protofibrils, for use as therapeutics or diagnostics.

The basic structure of an immunoglobulin (IgG) molecule comprises two identical light chains and two identical heavy chains linked together by disulphide bridges. The light chain, which is either lambda or kappa, has a variable region (VL) and a constant region (CL) of approximately 110 amino acid residues each. The heavy chain has a variable region (VH) of about 110 amino acid residues, but a much larger constant region (CH) of 300-400 amino acid residues, comprising CHγ1, CHγ2 and CHγ3 regions or domains.

The constant region (Fc) activates the complement system and binds to Fc receptors on macrophages, microglia and neutrophiles, which ingest and destroy infecting microorganisms or foreign/non-self antigens. This function is important since it is part of the therapeutic principle of the antibody, i.e. Fc receptor mediated microglial phagocytosis and clearance of α-synuclein protofibrils. Clearance of α-synuclein oligomeric intermediates via the lysosomal degradation pathway has been demonstrated (Lee et al., 2004). This process involves receptor-dependent or receptor-independent endocytosis of antibody/protofibril complexes, followed by fusion with lysosomes where the α-synuclein protofibrils are degraded (Masliah et al., 2005). Receptors that have been suggested to control this process include the Thy 1.1 receptor and the lipoprotein receptor-related protein (LPR).

Other anti-α-synuclein clearance mechanisms are likely to operate as well. The clearance of soluble α-synuclein protofibrils is a central mechanism of the treatment according to the invention. α-synuclein protofibrils are considered highly neurotoxic, initiating and driving the disease process. Clearance of α-synuclein protofibrils in the brain is of significant clinical value. In addition to clearance of α-synuclein protofibrils, other α-synuclein aggregated forms including α-synuclein fibrils, will be reduced indirectly via removal of the precursor forms to α-synuclein fibrils such as α-synuclein protofibrils, dimers, trimers, tetramers and higher oligomeric forms. Different α-synuclein forms including protofibrils and fibrils, are in equilibrium. Treatment with a high affinity protofibril binding antibody and clearance of α-synuclein protofibrils by said antibody will also have the advantage to indirectly reduce other α-synuclein aggregated or oligomeric forms. Yet another mechanism of action of the antibodies would be to block or inhibit α-synuclein toxicity by binding to toxic α-synuclein species and prevent their interactions with neurons.

The respective variable regions of the heavy and light chains contain three hyper variable regions called complementarity determining regions or CDRs. The CDR regions are short stretches of about 7-23, e.g. 13-23, amino acids, located in the VL and VH regions. The six CDRs regions on one "arm" of the antibody form the "pocket" that binds the antigen. Several definitions of CDR-sequences are used in the literature. SEQ ID NOS: 1-21 define the inventive CDR-sequences using a first identification system, and the thus identified CDR-sequences are shown in VL and VH in monoclonal antibodies specific for human wild-type and mutant α-synuclein protofibrils in Table 1 (see Example 2) by the underlined regions. SEQ ID NOS: 22-55 identify the inventive CDR-sequences using the known Kabat system, and the thus identified Kabat CDR-sequences are shown in VL and VH in antibodies specific for human wild-type and mutant α-synuclein protofibrils in Table 2 (see Example 2) by the underlined regions. The identification of the inventive CDR-sequences according to Kabat (SEQ ID NOS: 22-55) are used in the present disclosure.

Thus, in one embodiment, an antibody according to the invention is characterized by having the six CDR sequences (VH-CDR-1, VH-CDR-2, VH-CDR-3, VL-CDR-1, VL-CDR-2, and VL-CDR-3) selected from each of the following respective groups of CDR sequences, in any combination.

| VH CDR-1 | |
|---|---|
| GFTFNTYAM | SEQ ID NO: 1 |
| GFTFSNYAM | SEQ ID NO: 2 |
| GFTFSSYAM | SEQ ID NO: 3 |
| GDSFTSGYW | SEQ ID NO: 4 |
| GFTFNTYAMN | SEQ ID NO: 22 |
| GFTFSNYAMS | SEQ ID NO: 23 |
| GFTFSSYAMS | SEQ ID NO: 24 |
| GDSFTSGYWN | SEQ ID NO: 25 |
| GFSLTSYGVH | SEQ ID NO: 26 |
| GFTFTDYYMS | SEQ ID NO: 27 |

-continued

| VH CDR-2 | |
|---|---|
| RIRTKSNDYATYYADSVKG | SEQ ID NO: 5 |
| RIRTKSNDYATYYADSV | SEQ ID NO: 28 |
| TVTSGGSYTYYPDSVRG | SEQ ID NO: 6 |
| TVTSGGSYTYYPDSV | SEQ ID NO: 29 |
| TISNGGSYTYYPDSVKG | SEQ ID NO: 7 |
| TISNGGSYTYYPDSV | SEQ ID NO: 30 |
| YIRYSGNTYYNPSLKS | SEQ ID NO: 8 |
| YIRYSGNTYYNPSL | SEQ ID NO: 31 |
| VIWRGGSTDYSAAF | SEQ ID NO: 32 |
| TISTGGSYTYYPDSV | SEQ ID NO: 33 |
| FIRNKANGYTTEYSASV | SEQ ID NO: 34 |

| VH CDR-3 | |
|---|---|
| VGYRPYAMDY | SEQ ID NO: 9 (SEQ ID NO: 35) |
| QNFGSRGWYFDV | SEQ ID NO: 10 (SEQ ID NO: 36) |
| HSDYSGAWFAY | SEQ ID NO: 11 (SEQ ID NO: 37) |
| SYYDYDRAWFAY | SEQ ID NO: 12 (SEQ ID NO: 38) |
| LLRSVGGFAD | SEQ ID NO: 39 |
| DYGNYAMDY | SEQ ID NO: 40 |

| VL CDR-1 | |
|---|---|
| RSSQNIVHSNGNTYLE | SEQ ID NO: 13 (SEQ ID NO: 41) |
| RSSQSIVNSNGNTYLE | SEQ ID NO: 14 (SEQ ID NO: 42) |
| SASSSVSYMY | SEQ ID NO: 15 (SEQ ID NO: 43) |
| RSSQSLVHSNGNTYLH | SEQ ID NO: 16 (SEQ ID NO: 44) |
| RSSQTIVHNNGNTYLE | SEQ ID NO: 45 |
| KSSQSLLYSSNQKNYLA | SEQ ID NO: 46 |

| VL CDR-2 | |
|---|---|
| KVSNRFS | SEQ ID NO: 17 (SEQ ID NO: 47) |
| RTSNLAS | SEQ ID NO: 18 (SEQ ID NO: 48) |
| WASTRES | SEQ ID NO: 49 |

| VL CDR-3 | |
|---|---|
| FQGSHVPLT | SEQ ID NO: 19 (SEQ ID NO: 50) |
| QQYHSYPYT | SEQ ID NO: 20 (SEQ ID NO: 51) |
| SQSTHVPWT | SEQ ID NO: 21 (SEQ ID NO: 52) |
| FQGSHVPFT | SEQ ID NO: 53 |
| QQFHSYPYT | SEQ ID NO: 54 |
| QQYYSYPYT | SEQ ID NO: 55 |

One of the antibodies that was initially selected for certain interesting characteristics was rejected as it did not fulfil the criteria defining an antibody according to the present invention. An important parameter for this rejection was the comparatively short VH CDR-3 sequence with five amino acids exposed by this antibody. Therefore, it is concluded that the VH CDR-3 sequence needs to be more than 5 amino acids. In specific embodiments, the VH CDR-3 sequence is 9, 10, 11 or 12 amino acids.

In specific embodiments, the antibodies and fragments according to the invention have the six CDR sequences selected from the following combinations:
SEQ ID NOS: 22, 28, 35, 41, 47 and 50,
SEQ ID NOS: 23, 29, 36, 42, 47 and 50,
SEQ ID NOS: 24, 30, 37, 43, 48 and 51,
SEQ ID NOS: 25, 31, 38, 44, 47 and 52,
SEQ ID NOS: 26, 32, 39, 45, 47 and 53,
SEQ ID NOS: 23, 33, 37, 43, 48 and 54, and
SEQ ID NOS: 27, 34, 40, 46, 49 and 55.

In additional specific embodiments, antibodies providing desirable specificity for α-synuclein protofibrils while fulfilling other important characteristics defined herein have the six CDR sequences of the antibody or fragment selected from the following respective groups:
VH CDR-1 SEQ ID NOS: 23, 24, 25 or 26
VH CDR-2 SEQ ID NOS: 29, 30, 31 or 32
VH CDR-3 SEQ ID NO: 36
VL CDR-1 SEQ ID NOS: 42, 43, 44 or 45
VL CDR-2 SEQ ID NOS: 47 or 48
VL CDR-3 SEQ ID NOS: 50, 51, 52 or 53
or selected from the following respective groups:
VH CDR-1 SEQ ID NOS: 23, 24, 25 or 26
VH CDR-2 SEQ ID NOS: 29, 30, 31 or 32
VH CDR-3 SEQ ID NO: 37
VL CDR-1 SEQ ID NOS: 42, 43, 44 or 45
VL CDR-2 SEQ ID NOS: 47 or 48
VL CDR-3 SEQ ID NOS: 50, 51, 52 or 53
or selected from the following respective groups:
VH CDR-1 SEQ ID NOS: 23, 24, 25 or 26
VH CDR-2 SEQ ID NOS: 29, 30, 31 or 32
VH CDR-3 SEQ ID NO: 38
VL CDR-1 SEQ ID NOS: 42, 43, 44 or 45
VL CDR-2 SEQ ID NOS: 47 or 48
VL CDR-3 SEQ ID NOS: 50, 51, 52 or 53
or selected from the following respective groups:
VH CDR-1 SEQ ID NOS: 23, 24, 25 or 26
VH CDR-2 SEQ ID NOS: 29, 30, 31 or 32
VH CDR-3 SEQ ID NO: 39
VL CDR-1 SEQ ID NOS: 42, 43, 44 or 45
VL CDR-2 SEQ ID NOS: 47 or 48
VL CDR-3 SEQ ID NOS: 50, 51, 52 or 53.

As noted previously, the α-synuclein protofibril binding antibodies and fragments according to the invention are characterized by high affinity for the target. The high affinity, expressed as the dissociation constant $K_d$, is less than $10^{-7}$ M. In additional embodiments, the dissociation constant $K_d$ for human α-synuclein protofibrils is less than $10^{-8}$ M, less than $10^{-9}$ M, less than $10^{-10}$ M, or even less than $10^{-11}$ M. These antibodies and fragments have the advantage that they can be administered at lower doses compared to antibodies with affinities around $10^{-6}$ M or higher. This has a significant clinical advantage as these high affinity antibodies, which can be administered by injection, can be given subcutaneously since only a low amount of the antibody is needed to achieve efficacy. Administration modalities are not limited to subcutaneous or intravenous injections. Furthermore, the lower doses needed for efficacy will reduce cost of goods for production of the antibody.

In addition to the high affinity of the antibodies for α-synuclein protofibrils, the antibodies and fragments exhibit low binding to α-synuclein monomers, and optionally low binding to α-synuclein fibrils. As noted above, the low binding to α-synuclein monomers means that the binding of an antibody or fragment according to the invention to α-synuclein monomers is at least 100 times less than that to α-synuclein protofibrils. In more specific embodiments, the binding of an antibody or fragment according to the invention to α-synuclein protofibrils is more than 500 times or even more than 1000 times greater than that to α-synuclein monomers.

In another embodiment, the antibodies and fragments exhibit low binding to α-synuclein fibrils. In more specific embodiments, the binding of an antibody or fragment according to the invention to α-synuclein protofibrils is more than 100 times, more than 500 times, or even more than 1000 times, greater than that to α-synuclein fibrils.

In yet another embodiment of the invention, the antibodies and fragments exhibit low binding to beta amyloid (Aβ) protofibrils (e.g. $K_d > 10^{-5}$ M) and beta amyloid monomers (e.g. $K_d > 10^{-5}$ M).

In yet another embodiment of the invention, the antibodies and fragments exhibit low binding to β-synuclein monomer, γ-synuclein monomer, IAPP (islet amyloid polypeptide), and/or the Medin polypeptide, e.g. the binding of the antibodies and fragments is at least 100 times less to one or more of these peptides/proteins than that to the human α-synuclein protofibrils.

According to another embodiment of the invention, the antibody or fragment according to the present invention can be defined by the binding in a model system to a linear epitope in α-synuclein within the amino acid (aa) region 113-140, e.g. aa region 113-131, with aa 125-131, 121-124, 121-127, 121-131, 113-123 and 136-140 as examples of specific epitopes. In this model system, 15-mer α-synuclein peptides with an 11 amino acid sequence overlap are used (see Example 3 below).

According to an additional embodiment of the invention, an antibody or fragment is provided, having high affinity for human α-synuclein protofibrils and low binding of α-synuclein monomers, and comprising a combination of one CDR-sequence selected from each of the six CDR sequence groups of SEQ ID NOS: 22-27, 28-34, 35-40, 41-46, 47-49 and 50-52, and sequences having greater than 70, 80, 90, 95 or 98% similarity with any of said sequences in each respective group. The antibody or fragment binds to an epitope within the amino acid (aa) region 113-140, e.g. aa region 113-131, and in particular the epitopes aa 125-131, 121-124, 121-127, 121-131, 113-123 or 136-140, of immobilized linear α-synuclein in a model system comprising 15-mer α-synuclein peptides with 11 amino acids overlap.

According to another specific embodiment of the invention, the high affinity α-synuclein protofibril binding antibodies can reduce or inhibit α-synuclein aggregation, thereby reducing levels of soluble oligomeric α-synuclein forms in the brain.

According to another specific embodiment of the invention, the high affinity α-synuclein protofibril binding antibodies can bind α-synuclein oligomers/protofibrils outside the CNS as well, thereby shifting the equilibrium of said α-synuclein forms over the blood brain barrier in such a way as to lower CNS levels of said α-synuclein forms (drainage).

According to another specific embodiment of the invention, the antibodies are of IgG class, suitable for therapeutic use which can pass over the blood brain barrier. The high affinity α-synuclein protofibril binding IgG antibodies may be engineered to reduce complement factor C1q binding to the CH2 domain of IgG1 and reduce complement activation and risk of inflammation. This modification can be done in several different ways. One way is to make a chimeric antibody where the CHγ2 domain of the IgG1 constant region has been deleted and exchanged for the corresponding domain from IgG4 or part of the domain that confers C1q binding. It is well established that IgG4 does not bind C1q and hence does not activate the complement cascade. To achieve this, the constant region of the heavy chain (CH) is engineered is such a way as to combine the high affinity Fc-receptor domain (CHγ3) on IgG1 with the IgG4 domain (CHγ2) which has no binding for the complement factor C1q. This new antibody containing the chimeric constant heavy chain (IgG1:CHγ1, CHγ2:IgG4, CHγ3:IgG1) has the important properties of both efficient clearance of α-synuclein protofibrils through Fc-receptor mediated phagocytosis and reduced risk for side-effects, i.e., inflammation such as meningioencephalitis.

Yet another way of reducing the risk of inflammation is to alter the oligosaccharide structure of the antibody which will reduce complement factor C1q binding and complement activation. Thirty different structures of the complex biantennary oligosaccharides at Asn-297 in human IgG1 have been described. The absence of CH2 associated carbohydrates is believed to cause a conformational change in the "hinge" region of the antibody, reducing interaction efficacies with effector molecules and loss of complement activation function and C1q binding.

The modification of a high affinity human α-synuclein protofibril binding antibody by site-directed mutagenesis of Asn-297 to any other amino acid will generate an antibody of retained Fc-receptor binding with less C1q binding and hence reduced risk of inflammation, in particular at the blood brain barrier. An alternative to modify the glycosylation on the antibody is to express the antibody in a cell type where the enzyme N-acteylglucosaminyl-transferase I has been inactivated. This will yield an antibody with altered carbohydrate structure at Asn-297. A structure of $Man_5GlcNAc_2$, but not limited to this structure, is formed. This carbohydrate modification will reduce complement factor C1q binding and inhibit inflammation (Wright et al. 1998). Alternatively, aglycosylated protofibril binding antibodies can be achieved by culturing cells expressing antibodies in the presence of tunicamycin, which inhibits glycosylation. These antibodies will have altered complement activating activity as well as altered Fc-receptor function (Leatherbarrow et al. 1985). Screening of clones expressing antibodies with low complement activation and high Fc-receptor binding will generate protofibril binding antibodies that exhibit high Fc-mediated clearance of α-synuclein protofibrils and low C1q binding.

In another embodiment, the high affinity human α-synuclein protofibril binding antibody is of IgG subclass, e.g. IgG1 or IgG4, where the complement factor C1q binding site has been modified, i.e. Pro331>Ser331 (Xu et al. 1994), in such a way as to reduce or inhibit binding of complement factor C1q. Such antibodies are particularly suitable for administration, i.e., for the treatment, prevention or delaying onset of a neurodegenerative disorder with α-synuclein pathology, in an individual with such a disorder or at risk of developing such a disorder, for example, but not limited to, an individual having or at risk of developing PD. The proline residue at position 331 in human IgG1 can also be changed to a threonine or glycine or any other polar amino acid. This modification can be achieved by standard molecular biology techniques such as site-directed mutagenesis or DNA deletions.

Yet another aspect of the invention is the use of high affinity human α-synuclein protofibril binding antibodies to specifically determine protofibril levels in human or animal tissues, for example, in cerebrospinal fluid (CSF), blood, urine, saliva, or brain tissue, as a diagnostic tool or biomarker for, or for monitoring, a neurodegenerative disorder with α-synuclein pathology. Parkinson's disease (PD), dementia with Lewy bodies (DLB), the Lewy body variant of Alzheimer's disease, multiple system atrophy, psychosis, schizophrenia, and Creutzfeldt-Jakob disease are exemplary only of such neurodegenerative disorders with α-synuclein pathology. For example, levels of human α-synuclein protofibrils in CSF or blood of a PD patient are likely to be different as compared to a matched elderly control group not having Parkinson's disease or any other α-synucleinopathy. A person who is developing Parkinson's disease or any other α-synucleinopathy is likely to have altered levels of α-synuclein protofibril levels in CSF or blood compared to control subjects. Hence, determination of α-synuclein protofibril levels in CSF or blood can provide an early diagnosis of the disease. This is possible to achieve with the new high affinity α-synuclein protofibril binding antibodies according to the invention and, in a specific embodiment, may be achieved in combination with a sandwich ELISA method (see Example 5), where α-synuclein protofibrils have been determined down to 9 pM level. Interference of other α-synuclein forms, particularly α-synuclein monomers, and optionally α-synuclein fibrils and α-synuclein fragments in the assay, is negligible.

Examples of suitable methods for assaying α-synuclein protofibrils in these tissues as well as in cell cultures using an anti-α-synuclein protofibril antibody comprise immunoassays such as ELISA, RIA, Western blotting or dot blotting. These methods are suitable to follow treatment efficacy as measured by protofibril reduction in clinical trials and/or as a diagnostic test. Since α-synuclein protofibrils levels are very low in CSF and blood, the high affinity α-synuclein protofibril binding antibody of the invention is advantageous for a diagnostic test, for example, based on an ELISA method, to allow measurement of low levels of α-synuclein protofibrils.

According to such methods, the antibody or fragment according to the invention is added to a biological sample comprising or suspected of comprising α-synuclein protofibrils, and the presence of a complex formed between α-synuclein protofibril and the antibody or fragment is detected. The complex may be detected qualitatively, i.e., the presence of the complex is detected, or quantitatively, i.e., a concentration of the complex or a threshold concentration of the complex, may be detected, as desired.

In additional embodiments, the invention includes the use of the high affinity protofibril specific antibodies and fragments in imaging for detection, localization and quantitation of α-synuclein protofibrils in human and animal tissues. The antibody or fragment may be labelled with a detectable label, for example, a radioactive ligand such as $I^{131}$, $C^{14}$, $H^3$ or $Gallium^{68}$, but not limited to these radioisotopes, and contacted with a sample or administered for detection purposes. Such methods are suitable as a diagnostic tool for neurodegenerative disorders with α-synuclein pathology, including, but not limited to, Parkinson's disease, dementia with Lewy bodies and other α-synuclein related neurodegenerative disorders. In a specific embodiment, such methods may be conducted to monitor the development of an α-synuclein related disease in a subject without or under medication or other possible treatment.

Therefore, in one aspect of the invention the antibodies are added to a biological sample comprising or suspected of comprising α-synuclein protofibrils, the concentration of the complex formed between said protofibril and said antibody is measured for detection and/or quantification of protofibrils in the sample. In specific embodiments, the detection methods include immunoassay and proximity ligation assay. The biological sample may be an in vitro sample taken from a subject as well as an in vivo liquid volume.

Yet another aspect of the invention is to make the antibody species specific for use in veterinary medicine. The diagnostic methods outlined are also suitable for veterinary use.

Another aspect of the invention is the humanization of said antibodies to avoid side-effect, i.e. to avoid an immunoresponse against the antibodies in humans when used as a therapeutic or diagnostic agent. Such humanization techniques are within the ability of one of ordinary skill in the art.

The pharmaceutical compositions according to the invention comprise an antibody or fragment as described herein, and a pharmaceutically acceptable carrier. In a specific embodiment for therapeutic use, the compositions are physiologically acceptable formulations comprising a therapeutically active amount of an antibody or fragment according to the invention in a physiological buffer, for example, but not limited to, PBS, suitable for administration to humans and/or animals. The antibody or fragment can be freeze dried for better stability. The freeze dried formulation may contain any suitable conventional excipients, including stabilizers, lyoprotectants, buffers, and the like, such as, but not limited to, mannitol, for protecting and/or stabilizing the product during and/or after freeze drying and/or subsequent storage.

Optionally, the antibody formulation may contain an antibacterial agent or other preservative or additive which does not interfere with the function or efficacy of the protofibril binding antibody or fragment.

EXAMPLES

The following examples are provided for illustration and are not intended to limit the invention to these specific examples.

Example 1

α-Synuclein Protofibril Antibodies

Immunization/Polyclonal Antibodies

In the immunization scheme, Balb/C mice are utilized. As antigen, HNE stabilized α-synuclein protofibrils are used. These are produced as previously described (WO 2009/133521, incorporated herein by reference), with the following exception: a 60:1 ratio between HNE and α-synuclein is used. For immunization, mice are injected with HNE stabilized α-synuclein protofibrils and adjuvant (e.g. 3-6 times). One booster injection containing HNE-modified α-synuclein protofibrils was carried out prior to the mice being sacrificed. Blood from immunized mice was analyzed for reactivity toward α-synuclein protofibrils and α-synuclein monomers. The specificity of the polyclonal antibody response was analyzed by a direct ELISA. In a typical experiment, a flat bottom high binding 96-well polystyrene microtiter plate is coated with monomeric α-synuclein (unmodified or modified with HNE or other aldehydes), protofibrils/oligomeric α-synuclein (unmodified or modified with HNE or other aldehydes) or fibrillar α-synuclein, at a final concentration of 400 ng/well. The wells are blocked with 2% BSA, washed with 0.05% Tween-20/PBS and cell media supernatants (undiluted or diluted 1:1 with phosphate-buffered saline) from investigated polyclonal antibodies are added to the wells as primary antibodies. Alkaline phosphatase-conjugated goat anti-mouse mouse IgG/IgM antibody (Pierce Biotechnology, Rockford, Ill., USA) is used as the secondary antibody at a dilution of 1/1000 Immunoreactivity is visualized using p-nitrophenyl-phosphate (Sigma-Aldrich, MO, USA).

In the serum, antibodies that specifically recognize α-synuclein protofibrils/oligomers are detected. In addition, antibodies that recognize α-synuclein monomers can be found. The negative control represents a non-immunized mouse.

Hybridoma/Monoclonal Antibodies

Mouse B-cell hybridomas were used to produced monoclonal α-synuclein protofibril binding antibodies. Spleen cells are isolated and ground in sterile phosphate-buffered saline (PBS) and centrifuged at 1200×g for 10 min to collect a cell-rich pellet. The cells are further washed with PBS and centrifuged at 1200×g for 10 min. The cell pellet is resuspended in Dulbecco's minimum essential medium (DMEM, Invitrogen, La Jolla, Calif., USA) supplemented with 1% antibiotics. Spleen cells are mixed at 1:1 ratio with Sp2/0 cells (mouse myeloma cell line) in DMEM. To facilitate cell fusion, 1 ml of polyethylene glycol (Sigma-Aldrich, St. Louis, Mo., USA) is added to the cell mixture and the reaction is stopped with the addition of DMEM. Cells are harvested and the pellet is resuspended in DMEM supplemented with 10% (v/v) fetal bovine serum (Cambrex, Charles City, Iowa, USA) and also containing 1% (v/v) sodium pyruvate (Cambrex, Charles City, Iowa, USA), 1% (v/v) antibiotics (Sigma-Aldrich, St. Louis, Mo., USA) and 1% (v/v) L-glutamine (Cambrex, Charles City, Iowa, USA), 5% (v/v) BM condition media (Roche Diagnostics Scandinavia, Bromma, Sweden) and 2% (v/v) HAT media supplement (Sigma-Aldrich, St. Louis, Mo., USA). Cells are plated on 96 well cell culturing plates and allowed to rest and grow for 2 weeks.

Hybridoma cell supernatants are analysed in a direct ELISA. In a typical experiment, a flat bottom high binding 96 well polystyrene microtiter plate is coated with monomeric α-synuclein (unmodified or modified with HNE or other aldehydes), oligomeric/protofibrillar α-synuclein (unmodified or modified with HNE or other aldehydes) or fibrillar α-synuclein. The wells are blocked with 1% BSA, washed with PBS-Tween 20 (0.05%) and cell media supernatants (undiluted or diluted 1:2 or 1:5 with PBS-Tween 20 (0.05%)) from investigated hybridoma are added to the wells as primary antibodies. Horse radish peroxidase-conjugated HRP-coupled goat anti mouse Ig (Southern Biotechnology, prod. No. 1010-05) is used as the secondary antibody at a dilution of 1/5000. Immunoreactivity is visualized using K-Blue Aqueous TMB substrate (Neogen Corp. prod. No. 331177).

Example 2

Amino Acid Sequence of Variable Regions of Heavy Chain (VH) and Light Chain (VL/Vkappa) Monoclonal Antibodies Specific for α-Synuclein Protofibrils The amino acid sequences of the variable regions of heavy chain (VH) and light chain (VL), including the CDR regions of the antibodies were determined by RT PCR of mRNA template, followed by DNA sequencing. The amino acid sequences of the variable heavy chain region (VH) and the variable light chain region (VL) for selected antibodies are shown in Table 1. The positions of the CDR regions 1-3 are underlined and shown. The amino acid sequences of the CDR regions form the structural basis for binding human wild type and mutant α-synuclein protofibrils constituting the "pathogenic epitope" of α-synuclein protofibrils.

The amino acid sequences of the CDR regions 1-3 of the respective VL and VH chains for protofibril specific antibodies according to the invention are shown in Table 1. In Table 2 CDR-sequences of a series of additional antibodies according to the invention are included.

The combined amino acid sequences of the CDR1-3 regions of the VH and VL chains create the molecular "pocket" which binds human α-synuclein wild-type protofibrils with high affinity and specificity. This "pocket" forms the structural basis of the "PD/DLB epitope". Variations in the CDR amino acid sequence length are observed in both the VH chain and the VL chain and are compatible with binding to human α-synuclein protofibrils. A shorter CDR region provides a more restricted three dimensional structure of the binding pocket of the antibody, whereas a longer CDR region is more flexible.

The CDR sequences as shown in Tables 1 and 2 are embodiments of the present invention, as are the amino acid sequences in the "mouse framework" regions of the VH and VL chains, i.e., outside the CDR regions, as well as the human VL and VH framework regions for protofibril specific antibodies as, but not limited to, those.

Other amino acid substitutions in the CDR regions than what are shown in Tables 1 and 2 are compatible with high affinity and high specificity binding to human α-synuclein protofibrils. Where a polar amino acid is present in a particular position in a CDR region that particular amino acid can be substituted by another polar amino acid, with retained or improved high affinity and specificity binding to α-synuclein protofibrils. Likewise, if a non-polar or negatively or positively charged amino acid is present at a certain position, that amino acid can be substituted by a similar amino acid from the same polarity group.

As a particular amino acid or amino acids may exchanged in any position in the CDR regions by functional equivalents that confer substantially the same function and structure to the antibody with regard to affinity for α-synuclein protofibrils, such constructs are of course within the scope of the present invention. In this regard, antibodies and fragments having greater than 70, 80, 90, 95 or 98% similarity with one of the previously indicated VH CDR and VL CDR sequences of the respective groups, with the maintained epitope binding as described herein, are within the scope of the present invention.

TABLE 1

Amino acid sequence of variable regions of heavy chain (VH) and light chain (VL/Vkappa) from four different monoclonal antibodies specific for human wild-type and mutant α-synuclein protofibrils. Positions of the various CDR regions (1-3) are underlined in VL and VH Antibodies BA1-BA4 are examples of high affinity protofibril specific antibodies according to the invention.

VH-BA1: 49/G (SEQ ID NO: 56)
EVQLVETGGGLVQPKGSLKLSCATSGFTFNTYAMNWVRQAPGKGLEWVA
RIRTKSNDYATYYADSVKGRITISRDDSQSMLYLQMNNLKTEDT
AMYYCVAVGYRPYAMDYWGQGTSVTVSS

VH-BA2: 38E2/7 (SEQ ID NO: 57)
EVQLVESGGDLVKPGGSLKFSCARSGFTFSNYAMSWVRQTPDKRLEWVA
TVTSGGSYTYYPDSVRGRFTISRDNAKNTLYLQLSSLKSEDTAM
YFCARQNFGSRGWYFDVWGAGTTVTVSS

TABLE 1-continued

Amino acid sequence of variable regions of heavy chain (VH) and light chain (VL/Vkappa) from four different monoclonal antibodies specific for human wild-type and mutant α-synuclein protofibrils. Positions of the various CDR regions (1-3) are underlined in VL and VH Antibodies BA1-BA4 are examples of high affinity protofibril specific antibodies according to the invention.

VH-BA3: 38F11/2_8 (SEQ ID NO: 58)
EVMLVESGGGLVKPGGSLKLSCARSGFTFSSYAMSWVRQTPEKRLEWVA
TISNGGSYTYYPDSVKGRFTISRDNAKNTLYLQMSSLASEDTAM
YYCARHSDYSGAWFAYWGQGTLVTVSA

VH-BA4: 48B11/8 (SEQ ID NO: 59)
EVQLQESGPSLVKPSQTLSLTCSVTGDSFTSGYWNWIRKFPGNKLEYMG
YIRYSGNTYYNPSLKSRISITRDTSKNQYYLQLISVITEDTATF
YCARSYYDYDRAWFAYWGQGALVTVSA

Vkappa-BA1: 49/G (SEQ ID NO: 60)
DVLMTQTPLSLPVSLGDQASISCRSSQNIVHSNGNTYLEWYLQKPGQSPTLLIY
KVSNRFSGVPDRFSGSGSGTDFTLKISRVEAEDLGVYYC
FQGSHVPLTFGAGTKLELK Vkappa-BA2: 38E2/7 (SEQ ID NO: 61)
DVLMTQTPLSLPVSLGDQASISCRSSQSIVNSNGNTYLEWYLQKPGQSPKLLIY
KVSNRFSGVPDRFSGSGSGTDFTLKISRVEAEDLGVYYC
FQGSHVPLTFGAGTTLELK Vkappa-BA3: 38F11/2_8 (SEQ ID NO: 62)
QIVLTQSPAIMSASPGEKVTISCSASSSVSYMYWYQQKPGSSPKPWIYRTSNLASGVPARFSGSGSGTSYSLTISSMEAEDAATYYC
QQYHSY
PYTFGGGTKLEIK Vkappa-BA4: 48B11/8 (SEQ ID NO: 63)
DVVMTQTPLSLPVSLGDQASISCRSSQSLVHSNGNTYLHWYLQKPGQSPKLLIY
KVSNRFSGVPDRFSGSGSGTDFTLKISRVEAEDLGVYFC
SQSTHVPWTFGGGTKLEIK

TABLE 2

Amino acid sequences of variable regions of heavy chain and light chain from eight different antibodies specific for human wild-type and mutant α-synuclein protofibrils. Positions of the various CDR-regions according to the Kabat system are marked. The antibodies are examples of high affinity protofibril specific antibodies according to the invention. The Heavy Chains are respectively SEQ ID NOS: 64-71 and the Light Chains are respectively SEQ ID NOS: 72-79.

Heavy Chains

49/G
EVQLVETGGGLVQPKGSLKLSCATS<u>GFTFNTYAMN</u>WVRQAPGKGLEWVA<u>RIRTKSNDYAT</u>
<u>YYADSV</u>KGRITISRDDSQSMLYLQMNNLKTEDTAMYYCVR<u>VGYRPYA--MDY</u>WGQGTSVT
VSS

38E2/7
EVQLVESGGDLVKPGGSLKFSCAAS<u>GFTFSNYAMS</u>WVRQTPDKRLEWVA<u>TVTS--GGSYT</u>
<u>YYPDSV</u>RGRFTISRDNAKNTLYLQLSSLKSEDTAMYFCAR<u>QNFGSRGWYFDV</u>WGAGTTVT
VSS

38F11/2.8
EVMLVESGGGLVKPGGSLKLSCAAS<u>GFTFSSYAMS</u>WVRQTPEKRLEWVA<u>TISN--GGSYT</u>
<u>YYPDSV</u>KGRFTISRDNAKNTLYLQMSSLRSEDTAMYYCAR<u>HSDYSGAW--FAY</u>WGQGTKVT
VSA

48B11/8
EVQLQESGPSLVKPSQTLSLTCSVT<u>GDSFTSGYWN</u>WIRKFPGNKLEYMG<u>YIR--YSGNT</u>
<u>YYNPSL</u>KSRISITRDTSKNQYYLQLISVTTEDTATFYCARS<u>YYDYDRAWFAY</u>WGQGALVT
VSA

TABLE 2-continued

Amino acid sequences of variable regions of heavy chain and light chain from eight different antibodies specific for human wild-type and mutant α-synuclein protofibrils. Positions of the various CDR-regions according to the Kabat system are marked. The antibodies are examples of high affinity protofibril specific antibodies according to the invention. The Heavy Chains are respectively SEQ ID NOS: 64-71 and the Light Chains are respectively SEQ ID NOS: 72-79.

47E7/3.47     QVQLKQSGPSLVQPSQSLSITCSVSGFSLTSYGVHWVRLSPGKGLEWLGVIW---RGGST

DYSAAFMSRLSITKDNSKSQVFFKMSSLQADDTAIYYCAKLLRSVGG---FADWGQGTKVT

VSA

37D2/14       EVMLVESGGGLVKPGGSLKLSCAASGFTFSNYAMSWVRQTPEKRLEWVATIST---GGSYT

YYPDSVKRGFTISRDNANNALYLQMSSLRSEDTAMYYCARHSDYSGAW---FAYWGRGTLVT

VSA

43B9/1.4      EVQLQESGPSLVKPSQTLSLTCSVTGDSFTSGYWNWIRKFPGNKLEYMGYIR---YSGNT

YYNPSLKSRISITRDTSKNQYYLQLISVTTEDTATFYCARSYYDYDRAWFAYWGQGALVT

VSA

38E10/13.6.4  EVKLVESGGGLVQPGGSLRLSCATSGFTFTDYYMSWVRQPPGKALEWLGFIRNKANGYTT

EYSASVKGRFTISRDNSQSILYLQMNTLRAEDSATYYCARDYGNYA---MDYWGQGTSVT

VSS

Light Chains

49/G          DVLMTQTPLSLPVSLGDQASISCRSSQ-MIVHSNGNTYLEWYLQKPGQSPTLLIYKVSNR

FSGVPDRFSGSGSGTDFTLKISRVEAEDLGVYYCFQGSHVP------LTFGAGTKLELK

38E2/7        DVLMTQTPLSLPVSLGDQASISCRSSQ-SIVNSNGNTYLEWYLQKPGQSPKLLIYKVSNR

FSGVPDRGSGSGSGTDFTLKISRVEAEDLGVYYCFQGSHVP------LTFGAGTTLELK

38F11/2.8     QIVLTQSPAIMSASPGEKVTISCSASS------SVSYMYWYQQKPGSSPKPWIYRTSNL

ASGVPARFSGSGSGTSYSLTISSMEAEDAATYYCQQYHSYP------YTFGGGTLKEIK

48B11/8       DVVMTQTPLSLPVSLGDQASISCRSSQ-SLVHSNGNTYLEWYLQKPGQSPKLLIYKVSNR

FSGVPDRGSGSGSGTDFTLKISRVEAEDLGVYFCSQSTHVP------WTFGGGTKLEIK

47E7/3.47     DVLMTQTPLSLPVSLGDQASISCRSSQ-TIVHNNGNTYLEWYLQKPGQSPKLLIYKVSNR

FSGVPDRFSGSGSGTDFTLKISRVEAEDLGVYYCFQGSHVP------FTFGSGTKLEIK

37D2/14       QIVLTQSPAIMSASPGEKVTISCSASS------SVSYMYWYQQKPGSSPKPWIYRTSNL

ASGVPARFSGSGSGTSYSLTISSMEAEDAATYYCQQFHSYP------YTFGGGTKLEIK

43B9/1.4      DVVMTQTPLSLPVSLGDQASISCRSSQ-SLVHSNGNTYLHWYLQKPGQSPKLLIYKVSNR

FSGVPDRFSGSGSGTDFTLKISRVEAEDLGVYFCSQSTHVP------WTFGGGTKLEIK

38E10/13.6.4  DIVMSQSPSSLAVSVGEKVTMSCKSSQSLLYSSNQKNYLAWYQQKPGQSPKLLIYWASTR

ESGVPDRFTGSGSGTDFTLTISSVKAEDLAVYYCQQYYSYP------YTFGGGTKLEIK

CDRs 1-3 are highlighted.

Example 3

Epitope Mapping of α-Synuclein Protofibril Specific Monoclonal Antibodies

Epitope mappings of the antibodies were performed by immunoblotting on PepSpots membrane. Synthetic peptides spanning the entire sequence (amino acids 1-140) of human α-synuclein were custom synthesized by JPT Peptide Technologies (a subsidiary of Sigma Aldrich, UK) and immobilized on the PepSpots membrane. The 33 synthesised 15-mer peptides were designed with 11 amino acid sequence overlap. The peptides were covalently bound to a Whatman 50 cellulose membrane (Whatman, England) by the C-terminus and have usually an acetylated N-terminus due to a higher stability to degradation. The uncharged N-ac better represents the region in the native antigen then a charged NH3+-group. The results are set forth in Table 3.

TABLE 3

| Antibody | Epitope | Amino acid residue numbers of SEQ ID NO: 80 |
|---|---|---|
| 49/G | YEMPSEE | 125-131 |
| 38E2/7 | DNEAYEM | 121-127 |
| 38F11/2_8 | LEDMPVDPDNE | 113-123 |
| 48B11/8 | DNEA | 121-124 |
| 47E7/3_47 | DNEAYEM | 121-127 |
| 37D2/14 | LEDMPVDPDNE | 113-123 |
| 43B9/1_4 | YEPEA | 136-140 |
| 38E10/13_6_4 | DNEAYEMPSEE | 121-131 |

```
Human α-synuclein (SEQ ID NO: 80)
1         10        20        30        40        50
|         |         |         |         |         |
MDVFMKGLSKAKEGVVAAAEKTKQGVAEAAGKTKEGVLYVGSKTKEGVVH 51        60        70        80        90        100
|         |         |         |         |         |
GVATVAEKTKEQVTNVGGAVVTGVTAVAQKTVEGAGSIAAATGFVKKDQL 101       110       120       130       140
|         |         |         |         |
GKNEEGAPQEGILEDMPVDPDNEAYEMPSEEGYQDYEPEA
```

Alternatively, epitope mapping of the antibodies were performed by immunoblotting on PepSpots membrane (Sigma Aldrich) as follows: Synthetic peptides spanning the C-terminal sequence of human α-synuclein from amino acid 100 to 140 were custom synthesized and immobilized on the PepSpots membrane (Sigma Aldrich). The 30 synthesised 10-mer peptides were designed with 9 amino acid overlap. The results are shown in Table 4.

TABLE 4

| Antibody | Epitope | Amino acid residue numbers of SEQ ID NO: 80 |
|---|---|---|
| 38E2/7 | EAYEMP | 123-128 |
| 47E7/3_47 | NEAY | 122-125 |

Accordingly, the length and precise position of the epitope depends on the method used for determination.

Example 4

Characterization of High-Affinity Human α-Synuclein Protofibril Binding Monoclonal Antibodies by Competition ELISA This example shows four antibodies (mAb49/G, mAb38E2/7, mAb38F11/2_8 and mAb48B11/8). These antibodies show high affinity to α-synuclein protofibrils and low cross-reactivity (binding) to α-synuclein monomers, as measured by means of the competition ELISA assay described below. Briefly, the anti-α-synuclein antibody to be tested is allowed to interact in solution with α-synuclein monomers or protofibrils and thereafter the mix is added to a microtiter plate precoated with α-synuclein protofibrils. If the antibody binds to the antigen in the pre-incubation step, fewer antibodies will bind to the immobilized antigen on the microtiter plate. Antibody bound to the immobilized antigen is detected by an alkaline phosphates enzyme (ALP) conjugated secondary antibody. The conjugate is incubated with ALP substrate (pNPP) generating a yellow color that can be detected in a microtiter plate reader at 405 nm. Consequently, a low OD value reflects a high affinity of the antibody to the antigen in solution.

Specifically, a high-binding ELISA microtiter plate was coated with 100 µl/well of 1 µg/ml of α-synuclein protofibril, diluted in 1×PBS, sealed with adhesive sealer and incubated overnight at +4° C. Then, the coating solution was discarded and the residual binding capacity of the plate was blocked by adding 200 µl/well of PBS-Tween 20 (0.05%). The sealed plate was incubated for 60 min at room temperature (R.T.) by shaking at 900 rpm.

Meanwhile, peptide solution was prepared in 1×PBS-Tween 20 (0.05%) by diluting α-synuclein monomers or protofibril to a concentration of 140 nM. A 10-step 3× dilution series of α-synuclein monomers and protofibrils was performed in a volume of 50 µl in a round bottomed, low protein binding microtiter plate. To this solution, 50 µl of the tested antibody diluted in PBS-Tween 20 (0.05%) to a concentration of 100 ng/ml was added and allowed to interact for 60 min at R.T. by shaking at 900 rpm. Sub sequentially, these pre-incubated samples were added to the washed (3× wash) coated high-binding plate and allowed to incubate for 15 min at R.T. without shaking. The ELISA plate was then washed to remove unbound antibodies. Bound antibodies were detected with 100 µl of ALP-coupled anti-mouse-IgG (Mabtech, Sweden 3310-4) in diluted 1/1000 in PBS-Tween 20 (0.05%) incubated for 60 min at R.T. by shaking at 900 rpm.

Finally, the ELISA plate was washed to remove unbound antibodies and 100 µl of ALP-substrate were added to each well. The plate was kept dark during incubation at R.T. until a yellow color developed. Absorbance values were measured on continuous mode at a wavelength of 405 nm every 15 minutes up to 120 minutes. Measurements were used for IC50 determinations only if there was linearity between time and absorbance.

IC50 values were calculated as the concentration of either monomers or protofibrils needed to quench half of the signal in the ELISA. The concentration of either α-synuclein monomers or protofibrils used in this method was determined by means UV-SEC, using a commercial α-synuclein standard as reference (cat. S-1001-1, rPeptide, USA, 0.5 mg as determined with BCA). FIG. 1 shows the absorbance at 450 nm for the four protofibril specific monoclonal antibodies as determined by the described competition ELISA. The assay was performed with HNE-stabilized α-synuclein protofibrils.

Further ELISA experiments show that the candidate antibodies display the same affinity for human α-synuclein protofibrils stabilized by HNE or ONE. The antibodies also bind α-synuclein protofibrils/aggregates composed of A30P or A53T α-synuclein mutants stabilised by HNE as demonstrated by means of competition ELISA.

Figure 2A:
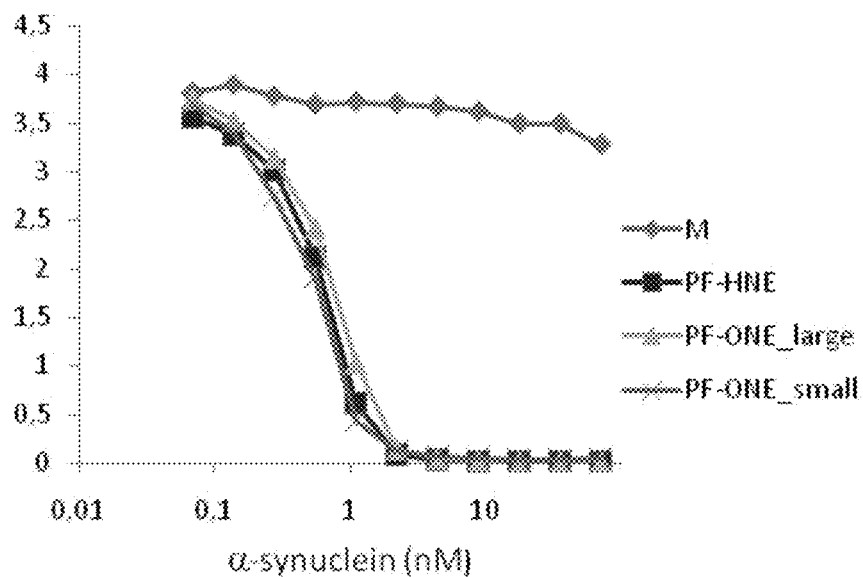
FIGS. 2A and 2B show the performance of protofibril specific antibody mAb49/G analyzed by a competition ELISA as described in Example 4.
Figure 2B:
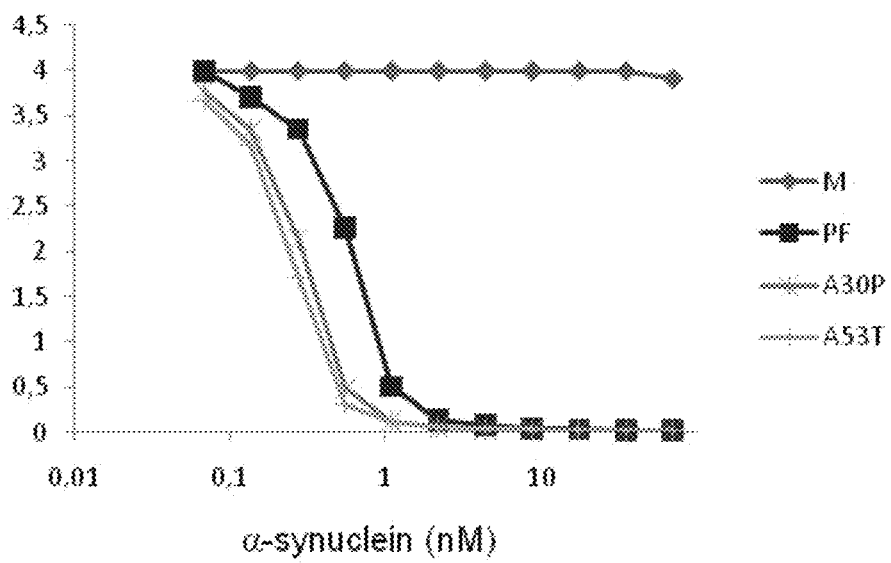

Specifically, FIGS. 2A and 2B show the results of the protofibril specific antibody mAb49/G analysed by a competition ELISA. Protofibril specific monoclonal antibody mAb49/G binds with high affinity to human α-synuclein protofibrils stabilized by either HNE or ONE (FIG. 2A). The monoclonal antibody also binds with high affinity to HNE-stabilized protofibrils of human mutated forms of α-synuclein, A30P and A53T (FIG. 2B). Aggregation of α-synuclein monomers with ONE generates two distinct populations of complexes, as defined by size exclusion chromatography. These two distinct peaks were separately eluted and labelled as FP-ONE_large and FP-ONE_small.

Figure 3A:
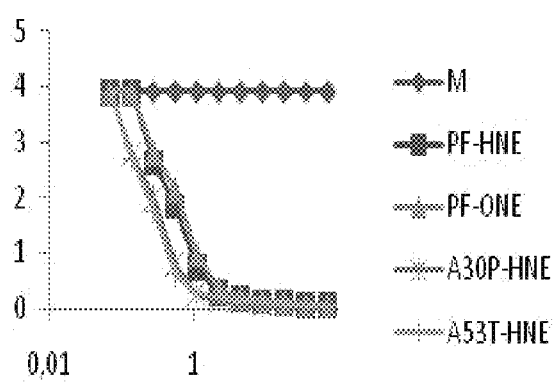
FIGS. 3A-3C show the performance of protofibril specific antibodies analyzed by a competition ELISA as described in Example 4. The protofibril specific monoclonal antibodies bind with high affinity to wild type human α-synuclein protofibrils stabilized by either HNE (PF-HNE) or ONE (PF-ONE). The monoclonal antibodies also bind with high affinity to HNE-stabilized protofibrils of human mutated forms of α-synuclein, A30P (A30P-HNE) and A53T (A30P-HNE).
Figure 3B:
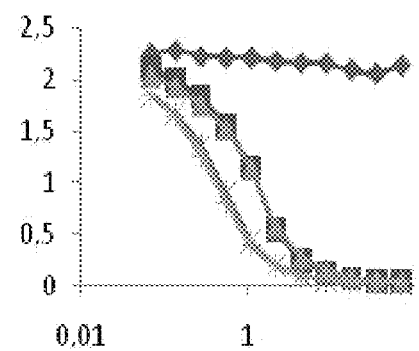
Figure 3C:
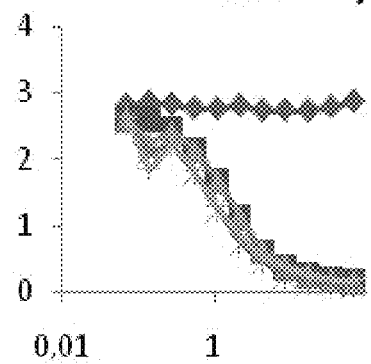

Additionally, FIGS. 3A-3C show the results of additional protofibril specific antibodies 38E2/7, 38F11/2_8 and 48B11/8, analysed by a competition ELISA. The protofibril specific monoclonal antibodies bind with high affinity to wild type human α-synuclein protofibrils stabilized by either HNE (PF-HNE) or ONE (PF-ONE). The monoclonal antibodies also bind with high affinity to HNE-stabilized protofibrils of human mutated forms of alpha synuclein, A30P (A30P-HNE) and A53T (A30P-HNE).

Example 5

Establishment of an α-Synuclein Protofibril Specific Sandwich ELISA

To enable measurements of α-synuclein protofibrils in biological samples, a sandwich ELISA with mAb49/G as both the capturing antibody and the detecting antibody was established. This assay measures α-synuclein protofibrils with limit of quantification LOQ=9 pM (see FIG. 4B). Due to uncertainties concerning the size of the α-synuclein protofibrils used in the standard curve, the concentration in pM is based on the molecular weight of one α-synuclein monomer (14,000 g/mol). Because the molecular weight of a protofibril has been estimated, by size exclusion chromatogarphy, to be at least 1,000,000 g/mol, the limit of detection calculated as molar α-synuclein protofibrils could be as low as 0.13 pM.

α-synuclein protofibrils stabilized by HNE and monomeric α-synuclein were used to validate the conformation specificity of the ELISA.

An ELISA composed of two identical antibodies requires at least a dimer of a protein to produce a signal. However, a large excess of monomeric α-synuclein, which may naturally occur in biological samples, could interfere with the α-synuclein protofibril analysis by occupying binding sites of the capture antibody coat, thus inhibiting the protofibrils from binding. This problem was investigated by adding an increasing excess of α-synuclein monomer to a fixed concentration of α-synuclein protofibrils (500 pM, expressed as monomer units) and analyzing it with the mAb49/G ELISA. A 30 000-fold molar excess of α-synuclein monomer (15 µM), as compared to α-synuclein protofibrils (500 pM), did not disturb the measurements with the mAb49/G sandwich ELISA, as expected since α-synuclein monomer binds poorly to the capture antibody.

Figure 4A:
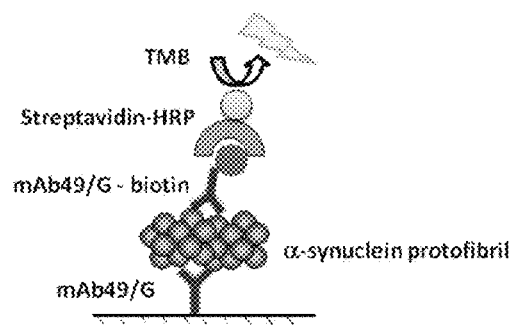
FIGS. 4A and 4B are directed to the quantification of α-synuclein protofibrils by sandwich ELISA as described in Example 5.
Figure 4B:
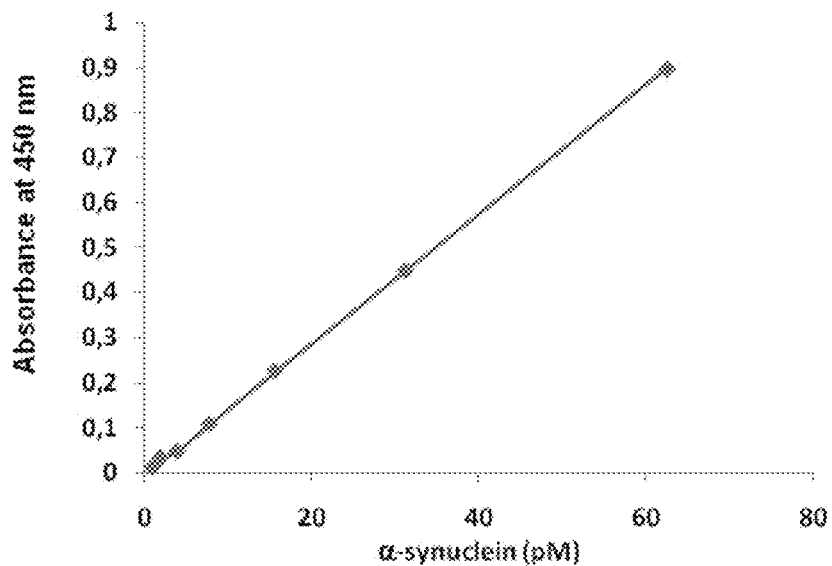

FIG. 4A shows a schematic illustration of the ELISA binding for quantification of α-synuclein protofibrils by sandwich ELISA. FIG. 4B shows the standard curve generated with HNE-stabilized α-synuclein protofibrils. The assay performance reached a limit of quantification, LOQ=9 pM.

Example 6

Figure 5A:
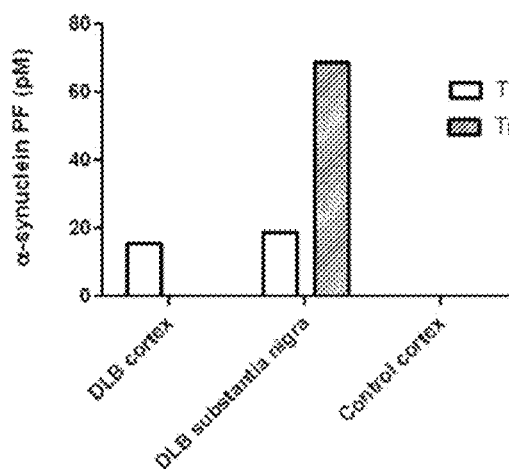
FIGS. 5A and 5B show the results of the analysis of diseased (DLB) and control human brain extracts with α-synuclein protofibril specific sandwich ELISA as described in Example 6.
Figure 5B:
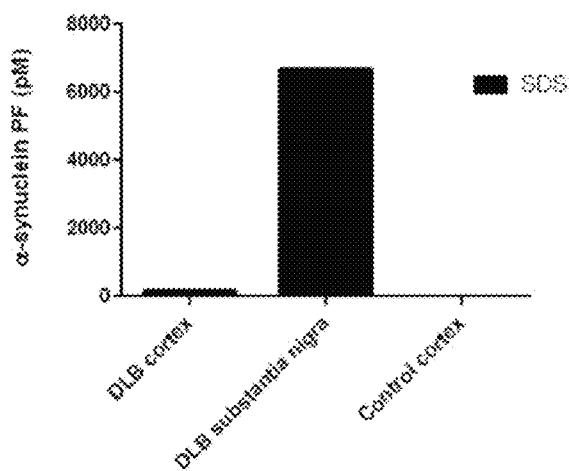

Analysis of Diseased and Control Human Brain Extracts with α-Synuclein Protofibril Specific Sandwich ELISA A brain extraction protocol using different detergents was performed, generating three different extracts: TBS extract (FIG. 5A, white bar) comprising extracellular and cytosolic α-synuclein species; Triton extract (FIG. 5A, striped bar) comprising membrane-associated α-synuclein species; and SDS extract (FIG. 5B, black bar), comprising SDS-soluble α-synuclein species. Brain extracts were analyzed from a patient diagnosed with the α-synucleinopathy dementia with lewy bodies (DLB). Brain tissue from cortex and substantia nigra was analyzed. As a control, brain tissue from cortex of a subject without detectable immunohistochemical Lewy body pathology was also analyzed. The sandwich ELISA was based on the α-synuclein protofibril specific mAb49/G as both the capturing antibody and the detection antibody. FIGS. 5A and 5B show the results of the analysis of diseased and control human brain extracts with α-synuclein protofibril specific sandwich ELISA. The assay allows for the quantification of protofibrils at levels >9 pM (limit of quantification; LOQ=9 pM).

Example 7

Measurement of α-Synuclein Protofibrils in Brain Extract from a PD Transgenic Mouse Model The presence of α-synuclein protofibrils in cell and mouse models have been suggested, though until now there has been no method for direct assaying of α-synuclein protofibrils in biological samples. The mAb49/G sandwich ELISA therefore provides the first opportunity to measure α-synuclein protofibril levels in biological samples and mouse models of α-synucleinopathies, characterised by the accumulation of aggregated α-synuclein.

Figure 6:
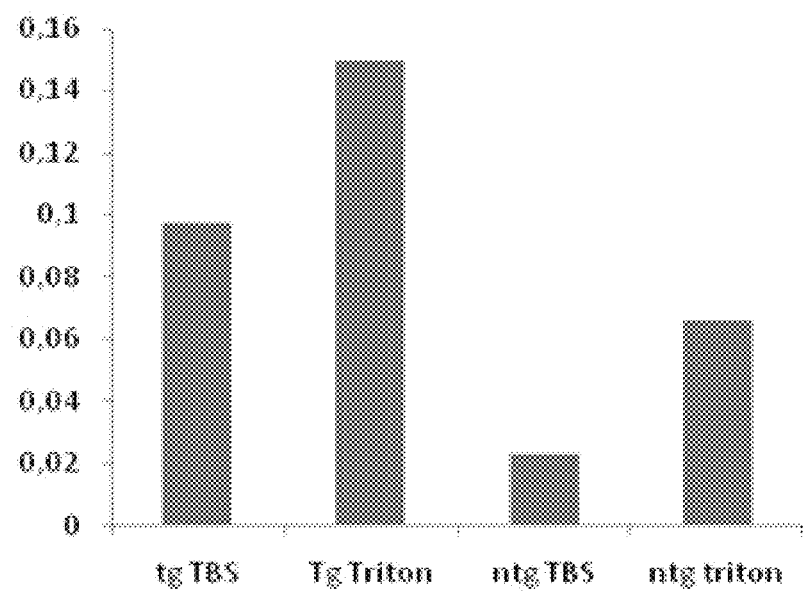
FIG. 6 shows analysis of brain extracts of control mice (ntg, non transgenic) and 5 month old mice from the Khale transgenic (tg) mouse PD model as described in Example 7. Brain tissue was extracted with tris buffered saline (TBS) and with TBS in the presence of Triton. Analysis was performed with α-synuclein protofibril sandwich ELISA as described in Example 5. Protofibril specific antibody mAb49/G was used as both the capturing antibody and the detection antibody. In the graph, the y axis represents the absorbance at OD450.

Brain extract samples from transgenic mice over-expressing human α-synuclein A53T mutant were compared with samples from wild type mice. Brains were homogenized in TBS or TBS+tween and centrifuged prior to analysis in order to recover the soluble α-synuclein fraction. Measurements of α-synuclein protofibril levels in the TBS-soluble fractions of non-transgenic mouse brain homogenates were compared to transgenic mice (Kahle model) (FIG. 6). To ensure that all α-synuclein measured in this assay was in a soluble state, all samples were centrifuged for 5 min at 16000×g before analysis. Levels of α-synuclein protofibrils were measured in brains from 5 month old transgenic mice with α-synuclein pathology.

FIG. 6 shows the results of the analysis of brain extracts of control mice (ntg, non transgenic) and 5 month old mice from Khale transgenic (tg) mouse PD model in which the y axis represents the absorbance at OD450.

Example 8

Immunohistochemical (IHC) Analysis of Human Brain Tissue

Cortex and substantia nigra from PD and DLB patients was used to perform immunohistochemical (IHC) analysis as described (Oinas et al. 2010). As control, cortex and substantia nigra from age-matched non-diseased patients was used. Positive antibody control for α-synuclein was a mouse anti-α-synuclein mAb (BD 610787).

Binding to Aβ plaques was evaluated as follows: two consecutive slides from the cortex of an AD patient were treated to display antigens and incubated with either a positive anti-Aβ mAb (mAb158, BioArctic) or with each one of the candidate antibodies. The bound antibody was detected by a secondary anti-species specific antibody coupled to horse radish peroxidase (HRP). The conjugate was then incubated with the HRP substrate DAB, generating a colored precipitate which was detected by light microscopy. The region in which Aβ plaques were detected by means of a colored precipitation in the positive control was analyzed in the co respective area in the slides treated with the candidate antibody. The lack of a colored precipitation was evaluated visually and interpreted as a lack of binding to Aβ plaques by the candidate antibodies.

Figure 7A:
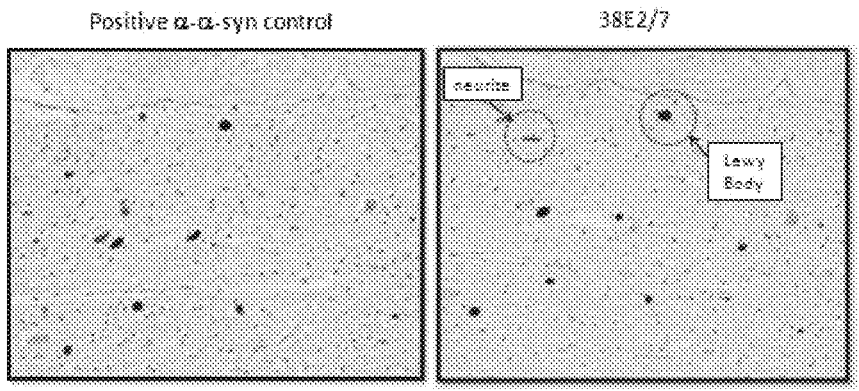
FIGS. 7A-7F show immunohistochemical (IHC) analysis of tissues as described in Example 8.
Figure 7B:
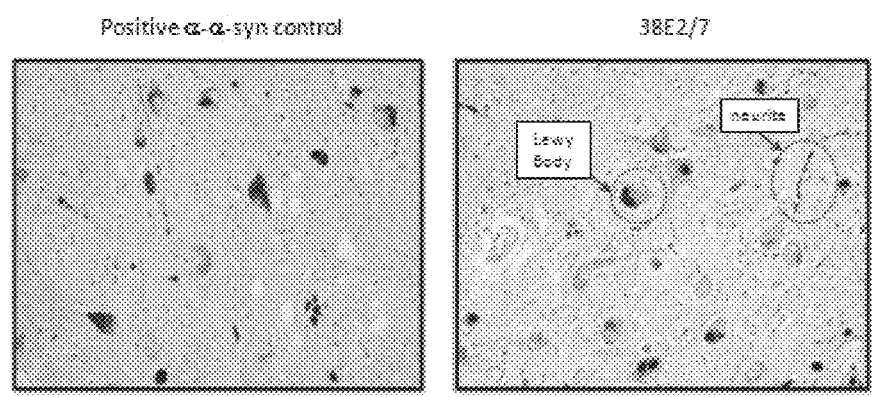
Figure 7C:
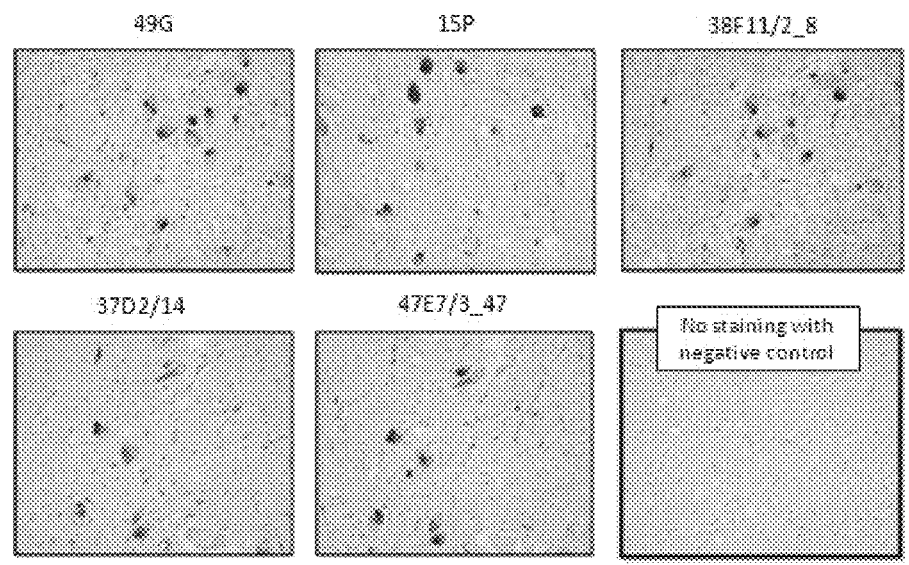
Figure 7D:
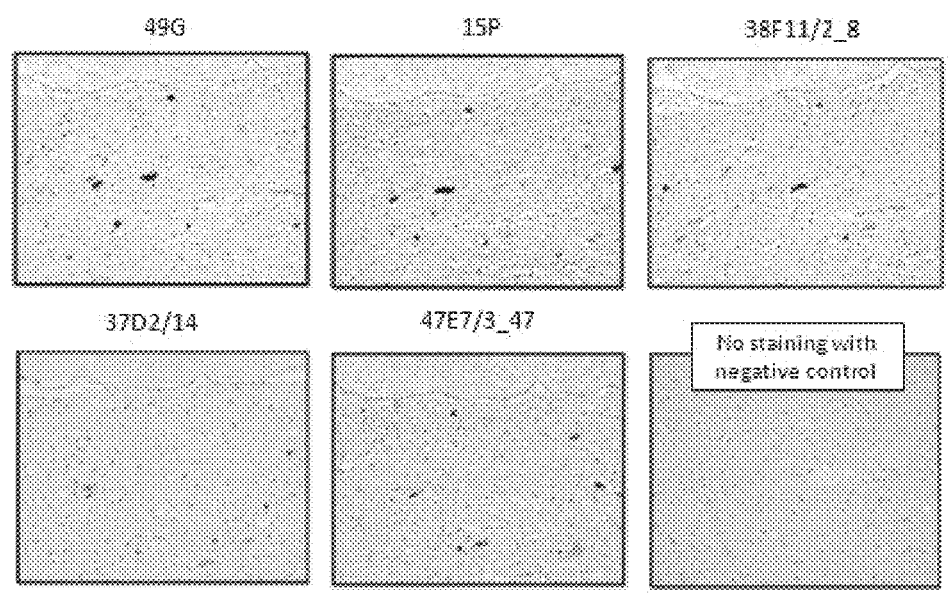
Figure 7E:
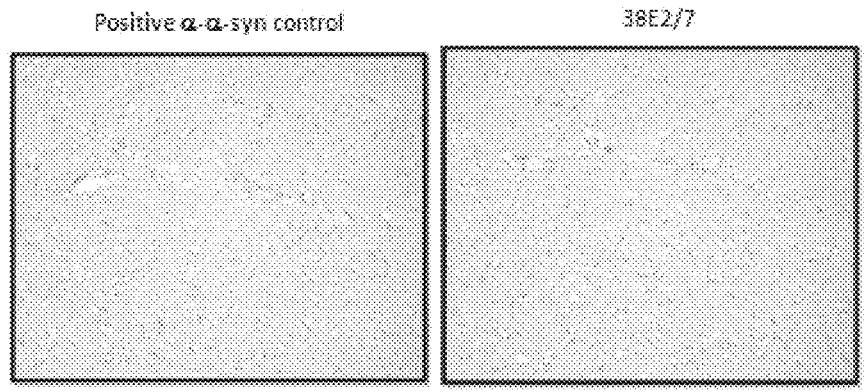
Figure 7F:
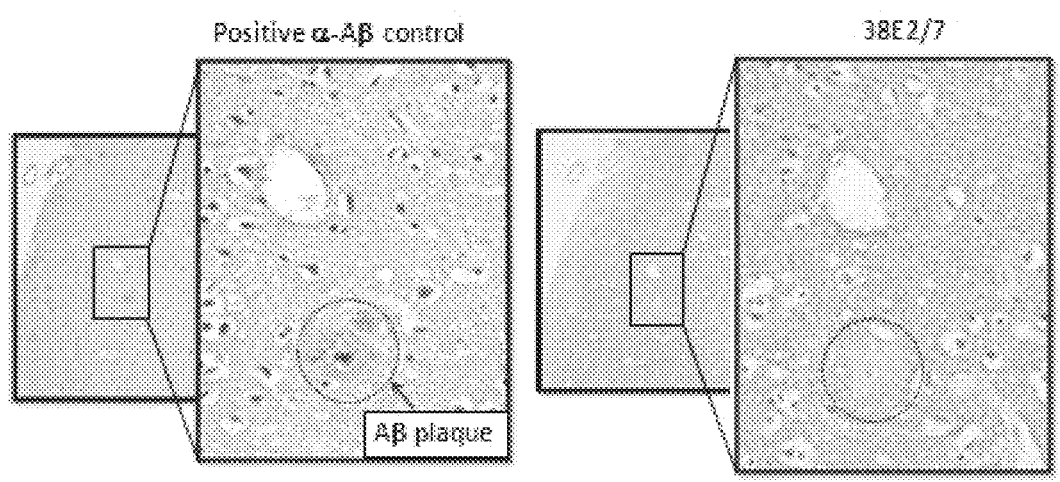

FIG. 7A shows 38E2/7 binding of Lewy bodies and neurites in PD substantia nigra and a positive α-α-synuclein control. FIG. 7B shows 38E2/7 binding of Lewy bodies and neurites in DLB cortex and substantia nigra and a positive α-α-synuclein control. FIG. 7C shows various antibodies binding Lewy bodies and neurites in DLB cortex and substantia nigra and a negative control. FIG. 7D shows various antibodies binding Lewy bodies and neurites in PD substantia nigra and a negative control. FIG. 7E shows no binding of 38E2/7 in non-disease related substantia nigra and a positive α-α-synuclein control. FIG. 7F shows a comparison of 38E2/7 binding and a positive α-Aβ control in cortex of an Alzheimer's disease patient.

Example 9

Analysis of Human Brain Extracts with Immunoprecipitation (IP) and Western Blot

Figure 8A:
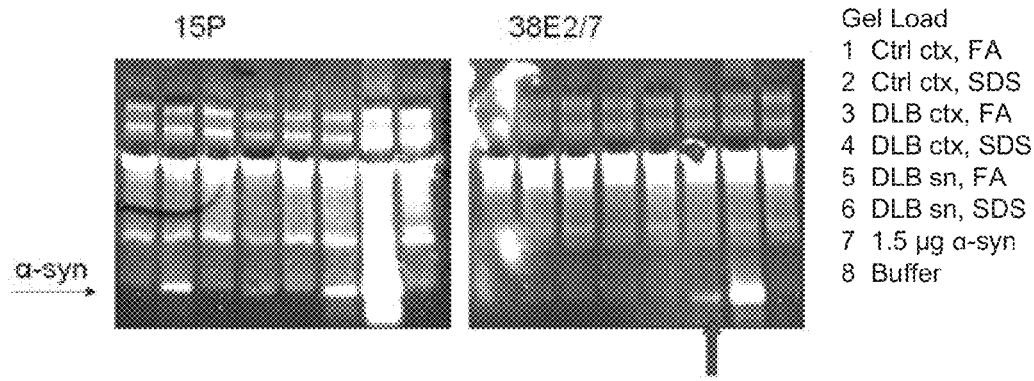
FIGS. 8A and 8B show the immunoprecipitation of human brain extracts with protofibril selective monoclonal antibody 38E2/7 using a brain extraction protocol as described in Example 9.
Figure 8B:
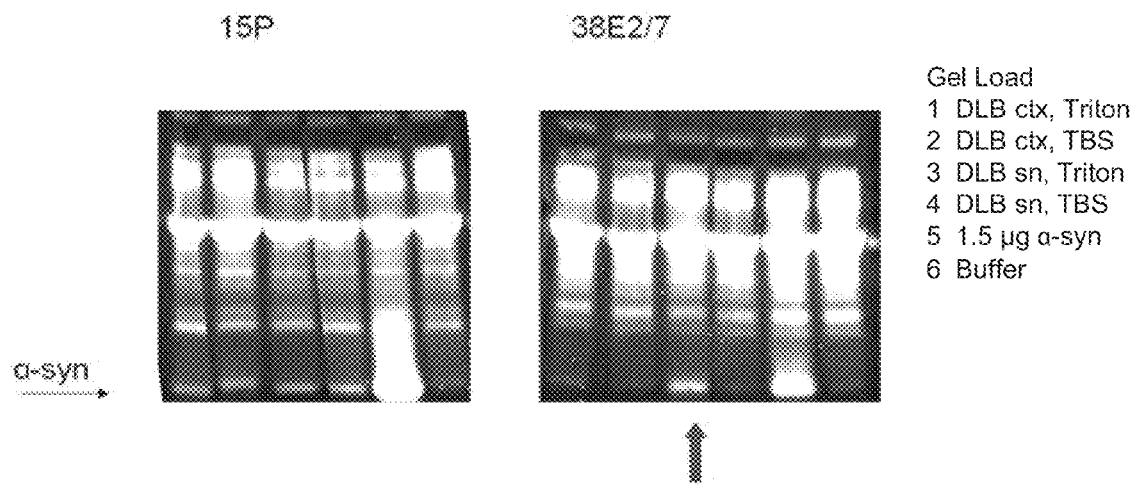

Immunoprecipitation of human brain extracts with protofibril binding monoclonal antibody 38E2/7 was conducted using western blot. A brain extraction protocol using different detergents was performed, generating four different extracts: TBS extract, comprising extracellular and cytosolic α-synuclein species; Triton extract, comprising membrane-associated α-synuclein species, SDS extract, comprising SDS-soluble α-synuclein species and FA extract, comprising insoluble α-synuclein. These extracts were immunoprecipitated with magnetic beads, to which antibody 38E2/7 or control antibody 15P were coupled. Antibody 15P can bind to α-synuclein protofibrils and monomers equally well and is expected to pull down all species presents. FIG. 8A shows SDS extract of substantia nigra of the DLB patient while FIG. 8B shows Triton extract of substantia nigra of the DLB patient. As seen, in FIGS. 8A and 8B, mAb 38E2/7 only captures α-synuclein protofibrils from DLB substantia nigra, both in the Triton and in the SDS extracts, whereas mAb15 captures α-synuclein monomers in all extracts.

Example 10

Analysis of α-Synuclein Oligomerization Inhibition

This example shows the antibody mAb49/G inhibits the oligomerization of α-synuclein monomers using an in vitro method in which neuronal cells are transfected with 2 vectors, both containing one copy of α-synuclein (aa 1-140) fused with either the N-terminal or the C-terminal fragment of GFP. Only those cells, in which α-synuclein has oligomerized, bringing both fragments of GFP together, will generate a green fluorescent color that can be detected with fluorescent microscopy. The presence of an antibody that can inhibit and/or disrupt oligomerization can be evaluated by comparing the fluorescence in these cultures, compared to a control to which no antibody as been added.

Specifically, H4 neuroglioma cells were transfected with equimolar ratios of DNA-constructs containing either α-synuclein (aa 1-140) fused with a N-terminal fragment of Green Fluorescent protein (GFP) (aa 1-155) or α-synuclein (aa 1-140) fused with a C-terminal fragment of GFP (aa 156-238) using the FuGENE 6 transfection reagent (Roche Diagnostics, Basel, Switzerland). Simultaneously, a control anti-α-synuclein monoclonal antibody (mAb5C2, Santa Cruz Bio) and mAb49/G were extracellularly added to the cells with a final concentration of 1 µg/ml. The cells were incubated for 24 hours in 37° C. in 5% $CO_2$. After 24 hours, the cells were moved to 30° C. for complete reconstitution of the GFP-fluorophore and incubated for an additional time of 24 hours. Fluorescence was measured using an Axiovert200 microscope equipped with a FITC epifluorescence filter. All data was calculated as relative % fluorescence intensity compared to antibody untreated α-synuclein over expressing cells, which was set to 100%.

As seen in the FIG. 9A, treatment with mAb49/G showed a significant (*$p<0.05$) reduction (42% decrease in fluorescence intensity compared to untreated cells) in α-synuclein oligomerization. FIG. 9B shows the results graphically as a percent fluorescence intensity compared to untreated α-synuclein overexpressing cells, which was set of 100%.

The specific examples and embodiments described herein are exemplary only in nature and are not intended to be limiting of the invention defined by the claims. Further embodiments and examples, and advantages thereof, will be apparent to one of ordinary skill in the art in view of this specification and are within the scope of the claimed invention.

REFERENCES

Chartier-Harlin, M C., et al. 2004. Alpha-synuclein locus duplication as a cause of familial Parkinson's disease. Lancet 1, 364,1167-1169.

Conway, K., et al., 2000. Acceleration of oligomerization, not fibrillization, is a shared property of both α-synuclein mutations linked to early-onset Parkinson's disease: Implications for pathogenesis and therapy. Proc Natl Acad Sci USA 97, 571-576.

Crews, L., et al., 2009. Role of synucleins in Alzheimer's disease. Neurotox Res. 16, 306-317.

Desplats, P., et al., 2009. Inclusion formation and neuronal cell death through neuron-to-neuron transmission of alpha-synuclein. Proc Natl Acad Sci USA. 4, 106, 13010-13015. Erratum in: Proc Natl Acad Sci USA. 2009, 106, 17606. Comment in: Proc Natl Acad Sci USA. 2009, 106, 12571-12572.

El-Agnaf, O. M., et al., 2006. Detection of oligomeric forms of α-synuclein protein in human plasma as a potential biomarker for Parkinson's disease. Faseb J 20, 419-425.

George, J. L., et al. 2009. Targeting the progression of Parkinson's disease. Curr Neuropharmacol. 7, 9-36.

Hansen, L, et al., 1990. The Lewy body variant of Alzheimer's disease. A clinical and pathologic entity. Neurology 40, 1-8.

Klucken, J., et al., 2006. Clinical and biochemical correlates of insoluble α-synuclein in dementia with Lewy bodies. Acta Neuropathol (Berl) 111, 101-108.

Kruger, R., et al., 1998. Ala30Pro mutation in the gene encoding α-synuclein in Parkinson's disease. Nat Genet. 18, 106-108.

Leatherbarrow, R. J., et al. 1985. Effector functions of a monoclonal aglycosylated mouse IgG2a: binding and activation of complement component C1 and interaction with human monocyte Fc receptor. Mol Immunol 22, 407-415.

Lee, H-J., et al. 2004. Clearance of α-synuclein oligomeric intermediates via the lysosomal degradation pathway. Journal of Neuroscience 24, 1888-1896.

Li, J. Y., et al Li et al. 2008. Lewy bodies in grafted neurons in subjects with Parkinson's disease suggest host-to-graft disease propagation Nature Med., 14, 501-503.

Masliah, E., et al. 2005. Effects of alpha-synuclein immunization in a mouse model of Parkinson's disease. Neuron. 46, 857-868.

Oinas, M., et al. 2010. alpha-Synuclein pathology in the spinal cord autonomic nuclei associates with alpha-synuclein pathology in the brain: a population-based Vantaa 85+ study. Acta Neuropathol. 119, 715-722.

Polymeropoulos, M. H., et al., 1997. Mutation in the α-Synuclein Gene Identified in Families with Parkinson's Disease. Science 276, 2045-2047.

Qin, Z., et al., 2007. Effect of 4-hydroxy-2-nonenal modification on α-synuclein aggregation. J Biol Chem 282, 5862-5870.

Singleton, A B., et al., 2003. alpha-Synuclein locus triplication causes Parkinson's disease. Science 302:841.

Wrigth, A., 1998. Effect of C2-associated carbohydrate structure on Ig effector function: studies with chimeric mouse-human IgG1 antibodies in glycosylation mutants of Chinese hamster ovary cells. J Immunol 160, 3393-3402.

Xu, Y., et al. 1994. Residue at position 331 in the IgG1 and IgG4 CH2 domains contributes to their differential ability to bind and activate complement. J Biol. Chem. 269, 3469-3474.

Yoritaka, A., et al., 1996 Immunohistochemical detection of 4-hydroxynonenal protein adducts in Parkinson disease. Proc Natl Acad Sci USA 93, 2696-2701.

Zarranz, J., et al., 2004. The new mutation, E46K, of α-synuclein causes Parkinson and Lewy body dementia. Ann Neurol. 55, 164-173.

What is claimed is:

1. A method of decreasing the amount of α-synuclein protofibrils in a subject, comprising administering to the individual an antibody or fragment thereof having high affinity for human α-synuclein protofibrils and low affinity for α-synuclein monomers and having a combination of three variable heavy (VH) CDR sequences and three variable light (VL) CDR sequences selected from the following combinations:
SEQ ID NOS: 22, 28, 35, 41, 47 and 50,
SEQ ID NOS: 23, 29, 36, 42, 47 and 50,
SEQ ID NOS: 24, 30, 37, 43, 48 and 51,
SEQ ID NOS: 25, 31, 38, 44, 47 and 52,
SEQ ID NOS: 26, 32, 39, 45, 47 and 53,
SEQ ID NOS: 23, 33, 37, 43, 48 and 54, and
SEQ ID NOS: 27, 34, 40, 46, 49 and 55.

2. The method of claim 1, wherein the antibody or fragment has a CDR sequence combination of SEQ ID NOS: 22, 28, 35, 41, 47 and 50.

3. The method of claim 1, wherein the antibody or fragment has a CDR sequence combination of SEQ ID NOS: 23, 29, 36, 42, 47 and 50.

4. The method of claim 1, wherein the antibody or fragment has a CDR sequence combination of SEQ ID NOS: 24, 30, 37, 43, 48 and 51.

5. The method of claim 1, wherein the antibody or fragment has a CDR sequence combination of SEQ ID NOS: 25, 31, 38, 44, 47 and 52.

6. The method of claim 1, wherein the antibody or fragment has a CDR sequence combination of SEQ ID NOS: 26, 32, 39, 45, 47 and 53.

7. The method of claim 1, wherein the antibody or fragment has a CDR sequence combination of SEQ ID NOS: 23, 33, 37, 43, 48 and 54.

8. The method of claim 1, wherein the antibody or fragment has a CDR sequence combination of SEQ ID NOS: 27, 34, 40, 46, 49 and 55.

9. A method of treating a neurodegenerative disorder with α-synuclein pathology in an individual, or delaying onset of a neurodegenerative disorder with α-synuclein pathology in an individual at risk of developing the disorder, wherein the disorder with α-synuclein pathology is characterized by deposition of Lewy bodies and Lewy neurites, comprising administering to the individual an antibody or fragment thereof having high affinity for human α-synuclein protofibrils and low affinity for α-synuclein monomers and having a combination of three variable heavy (VH) CDR sequences and three variable light (VL) CDR sequences selected from the following combinations:
SEQ ID NOS: 22, 28, 35, 41, 47 and 50,
SEQ ID NOS: 23, 29, 36, 42, 47 and 50,
SEQ ID NOS: 24, 30, 37, 43, 48 and 51,
SEQ ID NOS: 25, 31, 38, 44, 47 and 52,
SEQ ID NOS: 26, 32, 39, 45, 47 and 53,
SEQ ID NOS: 23, 33, 37, 43, 48 and 54, and
SEQ ID NOS: 27, 34, 40, 46, 49 and 55.

10. The method of claim 9, for delaying onset of the neurodegenerative disorder with α-synuclein pathology in an individual at risk of developing the disorder.

11. The method of claim 10, wherein the antibody or fragment has a CDR sequence combination of SEQ ID NOS: 22, 28, 35, 41, 47 and 50.

12. The method of claim 10, wherein the antibody or fragment has a CDR sequence combination of SEQ ID NOS: 23, 29, 36, 42, 47 and 50.

13. The method of claim 10, wherein the antibody or fragment has a CDR sequence combination of SEQ ID NOS: 24, 30, 37, 43, 48 and 51.

14. The method of claim 10, wherein the antibody or fragment has a CDR sequence combination of SEQ ID NOS: 25, 31, 38, 44, 47 and 52.

15. The method of claim 10, wherein the antibody or fragment has a CDR sequence combination of SEQ ID NOS: 26, 32, 39, 45, 47 and 53.

16. The method of claim 10, wherein the antibody or fragment has a CDR sequence combination of SEQ ID NOS: 23, 33, 37, 43, 48 and 54.

17. The method of claim 10, wherein the antibody or fragment has a CDR sequence combination of SEQ ID NOS: 27, 34, 40, 46, 49 and 55.

18. The method of claim 9, for treating the neurodegenerative disorder with α-synuclein pathology in an individual.

19. The method of claim 18, wherein the antibody or fragment has a CDR sequence combination of SEQ ID NOS: 22, 28, 35, 41, 47 and 50.

20. The method of claim 18, wherein the antibody or fragment has a CDR sequence combination of SEQ ID NOS: 23, 29, 36, 42, 47 and 50.

21. The method of claim 18, wherein the antibody or fragment has a CDR sequence combination of SEQ ID NOS: 24, 30, 37, 43, 48 and 51.

22. The method of claim 18, wherein the antibody or fragment has a CDR sequence combination of SEQ ID NOS: 25, 31, 38, 44, 47 and 52.

23. The method of claim 18, wherein the antibody or fragment has a CDR sequence combination of SEQ ID NOS: 26, 32, 39, 45, 47 and 53.

24. The method of claim 18, wherein the antibody or fragment has a CDR sequence combination of SEQ ID NOS: 23, 33, 37, 43, 48 and 54.

25. The method of claim 18, wherein the antibody or fragment has a CDR sequence combination of SEQ ID NOS: 27, 34, 40, 46, 49 and 55.

26. A method of treating a neurodegenerative disorder with α-synuclein pathology in an individual, or a delaying onset of a neurodegenerative disorder with α-synuclein pathology in an individual at risk of developing the disorder, wherein the disorder with α-synuclein pathology is selected from the group consisting of Parkinson's disease (PD), dementia with Lewy bodies (DLB), the Lewy body variant of Alzheimer's disease, and multiple system atrophy (MSA), comprising administering to the individual an antibody or fragment thereof having high affinity for human α-synuclein protofibrils and low affinity for α-synuclein monomers and having a combination of three variable heavy (VH) CDR sequences and three variable light (VL) CDR sequences selected from the following combinations:
SEQ ID NOS: 22, 28, 35, 41, 47 and 50,
SEQ ID NOS: 23, 29, 36, 42, 47 and 50,
SEQ ID NOS: 24, 30, 37, 43, 48 and 51,
SEQ ID NOS: 25, 31, 38, 44, 47 and 52,
SEQ ID NOS: 26, 32, 39, 45, 47 and 53,
SEQ ID NOS: 23, 33, 37, 43, 48 and 54, and
SEQ ID NOS: 27, 34, 40, 46, 49 and 55.

27. The method of claim 26, wherein the neurodegenerative disorder is dementia with Lewy bodies (DLB) or the Lewy body variant of Alzheimer's disease.

28. The method of claim 26, wherein the neurodegenerative disorder is the Lewy body variant of Alzheimer's disease.

29. The method of claim 26, wherein the neurodegenerative disorder is dementia with Lewy bodies (DLB).

30. The method of claim 26, wherein the neurodegenerative disorder is Parkinson's disease (PD).

31. The method of claim 30, wherein the antibody or fragment has a CDR sequence combination of SEQ ID NOS: 22, 28, 35, 41, 47 and 50.

32. The method of claim 30, wherein the antibody or fragment has a CDR sequence combination of SEQ ID NOS: 23, 29, 36, 42, 47 and 50.

33. The method of claim 30, wherein the antibody or fragment has a CDR sequence combination of SEQ ID NOS: 24, 30, 37, 43, 48 and 51.

34. The method of claim 30, wherein the antibody or fragment has a CDR sequence combination of SEQ ID NOS: 25, 31, 38, 44, 47 and 52.

35. The method of claim 30, wherein the antibody or fragment has a CDR sequence combination of SEQ ID NOS: 26, 32, 39, 45, 47 and 53.

36. The method of claim 30, wherein the antibody or fragment has a CDR sequence combination of SEQ ID NOS: 23, 33, 37, 43, 48 and 54.

37. The method of claim 30, wherein the antibody or fragment has a CDR sequence combination of SEQ ID NOS: 27, 34, 40, 46, 49 and 55.

38. The method of claim 26, wherein the antibody or fragment has low affinity for β-synuclein monomers.

39. The method of claim 26, wherein the antibody or fragment has low affinity for α-synuclein fibrils.

40. The method of claim 26, for delaying onset of the neurodegenerative disorder with α-synuclein pathology in an individual at risk for developing the disorder.

41. The method of claim 40, wherein the antibody or fragment has a CDR sequence combination of SEQ ID NOS: 22, 28, 35, 41, 47 and 50.

42. The method of claim 40, wherein the antibody or fragment has a CDR sequence combination of SEQ ID NOS: 23, 29, 36, 42, 47 and 50.

43. The method of claim 40, wherein the antibody or fragment has a CDR sequence combination of SEQ ID NOS: 24, 30, 37, 43, 48 and 51.

44. The method of claim 40, wherein the antibody or fragment has a CDR sequence combination of SEQ ID NOS: 25, 31, 38, 44, 47 and 52.

45. The method of claim 40, wherein the antibody or fragment has a CDR sequence combination of SEQ ID NOS: 26, 32, 39, 45, 47 and 53.

46. The method of claim 40, wherein the antibody or fragment has a CDR sequence combination of SEQ ID NOS: 23, 33, 37, 43, 48 and 54.

47. The method of claim 40, wherein the antibody or fragment has a CDR sequence combination of SEQ ID NOS: 27, 34, 40, 46, 49 and 55.

48. The method of claim 26, for treating the neurodegenerative disorder with α-synuclein pathology in an individual.

49. The method of claim 48, wherein the antibody or fragment has a CDR sequence combination of SEQ ID NOS: 22, 28, 35, 41, 47 and 50.

50. The method of claim 48, wherein the antibody or fragment has a CDR sequence combination of SEQ ID NOS: 23, 29, 36, 42, 47 and 50.

51. The method of claim 48, wherein the antibody or fragment has a CDR sequence combination of SEQ ID NOS: 24, 30, 37, 43, 48 and 51.

52. The method of claim 48, wherein the antibody or fragment has a CDR sequence combination of SEQ ID NOS: 25, 31, 38, 44, 47 and 52.

53. The method of claim 48, wherein the antibody or fragment has a CDR sequence combination of SEQ ID NOS: 26, 32, 39, 45, 47 and 53.

54. The method of claim 48, wherein the antibody or fragment has a CDR sequence combination of SEQ ID NOS: 23, 33, 37, 43, 48 and 54.

55. The method of claim 48, wherein the antibody or fragment has a CDR sequence combination of SEQ ID NOS: 27, 34, 40, 46, 49 and 55.

* * * * *

SEQUENCE LISTING

```
<160> NUMBER OF SEQ ID NOS: 80

<210> SEQ ID NO 1
<211> LENGTH: 9
<212> TYPE: PRT
<213> ORGANISM: Homo sapiens

<400> SEQUENCE: 1

Gly Phe Thr Phe Asn Thr Tyr Ala Met
1               5

<210> SEQ ID NO 2
<211> LENGTH: 9
<212> TYPE: PRT
<213> ORGANISM: Homo sapiens

<400> SEQUENCE: 2

Gly Phe Thr Phe Ser Asn Tyr Ala Met
1               5

<210> SEQ ID NO 3
<211> LENGTH: 9
<212> TYPE: PRT
<213> ORGANISM: Homo sapiens

<400> SEQUENCE: 3

Gly Phe Thr Phe Ser Ser Tyr Ala Met
1               5

<210> SEQ ID NO 4
<211> LENGTH: 9
<212> TYPE: PRT
<213> ORGANISM: Homo sapiens

<400> SEQUENCE: 4

Gly Asp Ser Phe Thr Ser Gly Tyr Trp
1               5

<210> SEQ ID NO 5
<211> LENGTH: 19
<212> TYPE: PRT
<213> ORGANISM: Homo sapiens

<400> SEQUENCE: 5

Arg Ile Arg Thr Lys Ser Asn Asp Tyr Ala Thr Tyr Tyr Ala Asp Ser
1               5                   10                  15

Val Lys Gly
```

```
<210> SEQ ID NO 6
<211> LENGTH: 17
<212> TYPE: PRT
<213> ORGANISM: Homo sapiens

<400> SEQUENCE: 6

Thr Val Thr Ser Gly Gly Ser Tyr Thr Tyr Tyr Pro Asp Ser Val Arg
1               5                   10                  15

Gly

<210> SEQ ID NO 7
<211> LENGTH: 17
<212> TYPE: PRT
<213> ORGANISM: Homo sapiens

<400> SEQUENCE: 7

Thr Ile Ser Asn Gly Gly Ser Tyr Thr Tyr Tyr Pro Asp Ser Val Lys
1               5                   10                  15

Gly

<210> SEQ ID NO 8
<211> LENGTH: 16
<212> TYPE: PRT
<213> ORGANISM: Homo sapiens

<400> SEQUENCE: 8

Tyr Ile Arg Tyr Ser Gly Asn Thr Tyr Tyr Asn Pro Ser Leu Lys Ser
1               5                   10                  15

<210> SEQ ID NO 9
<211> LENGTH: 10
<212> TYPE: PRT
<213> ORGANISM: Homo sapiens

<400> SEQUENCE: 9

Val Gly Tyr Arg Pro Tyr Ala Met Asp Tyr
1               5                   10

<210> SEQ ID NO 10
<211> LENGTH: 12
<212> TYPE: PRT
<213> ORGANISM: Homo sapiens

<400> SEQUENCE: 10

Gln Asn Phe Gly Ser Arg Gly Trp Tyr Phe Asp Val
1               5                   10

<210> SEQ ID NO 11
<211> LENGTH: 11
<212> TYPE: PRT
<213> ORGANISM: Homo sapiens

<400> SEQUENCE: 11

His Ser Asp Tyr Ser Gly Ala Trp Phe Ala Tyr
1               5                   10

<210> SEQ ID NO 12
<211> LENGTH: 12
<212> TYPE: PRT
<213> ORGANISM: Homo sapiens

<400> SEQUENCE: 12
```

```
Ser Tyr Tyr Asp Tyr Asp Arg Ala Trp Phe Ala Tyr
1               5                   10
```

<210> SEQ ID NO 13
<211> LENGTH: 16
<212> TYPE: PRT
<213> ORGANISM: Homo sapiens

<400> SEQUENCE: 13

```
Arg Ser Ser Gln Asn Ile Val His Ser Asn Gly Asn Thr Tyr Leu Glu
1               5                   10                  15
```

<210> SEQ ID NO 14
<211> LENGTH: 16
<212> TYPE: PRT
<213> ORGANISM: Homo sapiens

<400> SEQUENCE: 14

```
Arg Ser Ser Gln Ser Ile Val Asn Ser Asn Gly Asn Thr Tyr Leu Glu
1               5                   10                  15
```

<210> SEQ ID NO 15
<211> LENGTH: 10
<212> TYPE: PRT
<213> ORGANISM: Homo sapiens

<400> SEQUENCE: 15

```
Ser Ala Ser Ser Ser Val Ser Tyr Met Tyr
1               5                   10
```

<210> SEQ ID NO 16
<211> LENGTH: 16
<212> TYPE: PRT
<213> ORGANISM: Homo sapiens

<400> SEQUENCE: 16

```
Arg Ser Ser Gln Ser Leu Val His Ser Asn Gly Asn Thr Tyr Leu His
1               5                   10                  15
```

<210> SEQ ID NO 17
<211> LENGTH: 7
<212> TYPE: PRT
<213> ORGANISM: Homo sapiens

<400> SEQUENCE: 17

```
Lys Val Ser Asn Arg Phe Ser
1               5
```

<210> SEQ ID NO 18
<211> LENGTH: 7
<212> TYPE: PRT
<213> ORGANISM: Homo sapiens

<400> SEQUENCE: 18

```
Arg Thr Ser Asn Leu Ala Ser
1               5
```

<210> SEQ ID NO 19
<211> LENGTH: 9
<212> TYPE: PRT
<213> ORGANISM: Homo sapiens

<400> SEQUENCE: 19

```
Phe Gln Gly Ser His Val Pro Leu Thr
1               5
```

<210> SEQ ID NO 20
<211> LENGTH: 9
<212> TYPE: PRT
<213> ORGANISM: Homo sapiens

<400> SEQUENCE: 20

Gln Gln Tyr His Ser Tyr Pro Tyr Thr
1               5

<210> SEQ ID NO 21
<211> LENGTH: 9
<212> TYPE: PRT
<213> ORGANISM: Homo sapiens

<400> SEQUENCE: 21

Ser Gln Ser Thr His Val Pro Trp Thr
1               5

<210> SEQ ID NO 22
<211> LENGTH: 10
<212> TYPE: PRT
<213> ORGANISM: Homo sapiens

<400> SEQUENCE: 22

Gly Phe Thr Phe Asn Thr Tyr Ala Met Asn
1               5                   10

<210> SEQ ID NO 23
<211> LENGTH: 10
<212> TYPE: PRT
<213> ORGANISM: Homo sapiens

<400> SEQUENCE: 23

Gly Phe Thr Phe Ser Asn Tyr Ala Met Ser
1               5                   10

<210> SEQ ID NO 24
<211> LENGTH: 10
<212> TYPE: PRT
<213> ORGANISM: Homo sapiens

<400> SEQUENCE: 24

Gly Phe Thr Phe Ser Ser Tyr Ala Met Ser
1               5                   10

<210> SEQ ID NO 25
<211> LENGTH: 10
<212> TYPE: PRT
<213> ORGANISM: Homo sapiens

<400> SEQUENCE: 25

Gly Asp Ser Phe Thr Ser Gly Tyr Trp Asn
1               5                   10

<210> SEQ ID NO 26
<211> LENGTH: 10
<212> TYPE: PRT
<213> ORGANISM: Homo sapiens

<400> SEQUENCE: 26

Gly Phe Ser Leu Thr Ser Tyr Gly Val His
1               5                   10

```
<210> SEQ ID NO 27
<211> LENGTH: 10
<212> TYPE: PRT
<213> ORGANISM: Homo sapiens

<400> SEQUENCE: 27

Gly Phe Thr Phe Thr Asp Tyr Tyr Met Ser
1               5                   10

<210> SEQ ID NO 28
<211> LENGTH: 17
<212> TYPE: PRT
<213> ORGANISM: Homo sapiens

<400> SEQUENCE: 28

Arg Ile Arg Thr Lys Ser Asn Asp Tyr Ala Thr Tyr Tyr Ala Asp Ser
1               5                   10                  15

Val

<210> SEQ ID NO 29
<211> LENGTH: 15
<212> TYPE: PRT
<213> ORGANISM: Homo sapiens

<400> SEQUENCE: 29

Thr Val Thr Ser Gly Gly Ser Tyr Thr Tyr Tyr Pro Asp Ser Val
1               5                   10                  15

<210> SEQ ID NO 30
<211> LENGTH: 15
<212> TYPE: PRT
<213> ORGANISM: Homo sapiens

<400> SEQUENCE: 30

Thr Ile Ser Asn Gly Gly Ser Tyr Thr Tyr Tyr Pro Asp Ser Val
1               5                   10                  15

<210> SEQ ID NO 31
<211> LENGTH: 14
<212> TYPE: PRT
<213> ORGANISM: Homo sapiens

<400> SEQUENCE: 31

Tyr Ile Arg Tyr Ser Gly Asn Thr Tyr Tyr Asn Pro Ser Leu
1               5                   10

<210> SEQ ID NO 32
<211> LENGTH: 14
<212> TYPE: PRT
<213> ORGANISM: Homo sapiens

<400> SEQUENCE: 32

Val Ile Trp Arg Gly Gly Ser Thr Asp Tyr Ser Ala Ala Phe
1               5                   10

<210> SEQ ID NO 33
<211> LENGTH: 15
<212> TYPE: PRT
<213> ORGANISM: Homo sapiens

<400> SEQUENCE: 33

Thr Ile Ser Thr Gly Gly Ser Tyr Thr Tyr Tyr Pro Asp Ser Val
1               5                   10                  15
```

```
<210> SEQ ID NO 34
<211> LENGTH: 17
<212> TYPE: PRT
<213> ORGANISM: Homo sapiens

<400> SEQUENCE: 34

Phe Ile Arg Asn Lys Ala Asn Gly Tyr Thr Thr Glu Tyr Ser Ala Ser
1               5                   10                  15
Val

<210> SEQ ID NO 35
<211> LENGTH: 10
<212> TYPE: PRT
<213> ORGANISM: Homo sapiens

<400> SEQUENCE: 35

Val Gly Tyr Arg Pro Tyr Ala Met Asp Tyr
1               5                   10

<210> SEQ ID NO 36
<211> LENGTH: 12
<212> TYPE: PRT
<213> ORGANISM: Homo sapiens

<400> SEQUENCE: 36

Gln Asn Phe Gly Ser Arg Gly Trp Tyr Phe Asp Val
1               5                   10

<210> SEQ ID NO 37
<211> LENGTH: 11
<212> TYPE: PRT
<213> ORGANISM: Homo sapiens

<400> SEQUENCE: 37

His Ser Asp Tyr Ser Gly Ala Trp Phe Ala Tyr
1               5                   10

<210> SEQ ID NO 38
<211> LENGTH: 12
<212> TYPE: PRT
<213> ORGANISM: Homo sapiens

<400> SEQUENCE: 38

Ser Tyr Tyr Asp Tyr Asp Arg Ala Trp Phe Ala Tyr
1               5                   10

<210> SEQ ID NO 39
<211> LENGTH: 10
<212> TYPE: PRT
<213> ORGANISM: Homo sapiens

<400> SEQUENCE: 39

Leu Leu Arg Ser Val Gly Gly Phe Ala Asp
1               5                   10

<210> SEQ ID NO 40
<211> LENGTH: 9
<212> TYPE: PRT
<213> ORGANISM: Homo sapiens

<400> SEQUENCE: 40

Asp Tyr Gly Asn Tyr Ala Met Asp Tyr
1               5
```

```
<210> SEQ ID NO 41
<211> LENGTH: 16
<212> TYPE: PRT
<213> ORGANISM: Homo sapiens

<400> SEQUENCE: 41

Arg Ser Ser Gln Asn Ile Val His Ser Asn Gly Asn Thr Tyr Leu Glu
1               5                   10                  15

<210> SEQ ID NO 42
<211> LENGTH: 16
<212> TYPE: PRT
<213> ORGANISM: Homo sapiens

<400> SEQUENCE: 42

Arg Ser Ser Gln Ser Ile Val Asn Ser Asn Gly Asn Thr Tyr Leu Glu
1               5                   10                  15

<210> SEQ ID NO 43
<211> LENGTH: 10
<212> TYPE: PRT
<213> ORGANISM: Homo sapiens

<400> SEQUENCE: 43

Ser Ala Ser Ser Ser Val Ser Tyr Met Tyr
1               5                   10

<210> SEQ ID NO 44
<211> LENGTH: 16
<212> TYPE: PRT
<213> ORGANISM: Homo sapiens

<400> SEQUENCE: 44

Arg Ser Ser Gln Ser Leu Val His Ser Asn Gly Asn Thr Tyr Leu His
1               5                   10                  15

<210> SEQ ID NO 45
<211> LENGTH: 16
<212> TYPE: PRT
<213> ORGANISM: Homo sapiens

<400> SEQUENCE: 45

Arg Ser Ser Gln Thr Ile Val His Asn Gly Asn Thr Tyr Leu Glu
1               5                   10                  15

<210> SEQ ID NO 46
<211> LENGTH: 17
<212> TYPE: PRT
<213> ORGANISM: Homo sapiens

<400> SEQUENCE: 46

Lys Ser Ser Gln Ser Leu Leu Tyr Ser Ser Asn Gln Lys Asn Tyr Leu
1               5                   10                  15

Ala

<210> SEQ ID NO 47
<211> LENGTH: 7
<212> TYPE: PRT
<213> ORGANISM: Homo sapiens

<400> SEQUENCE: 47

Lys Val Ser Asn Arg Phe Ser
1               5
```

```
<210> SEQ ID NO 48
<211> LENGTH: 7
<212> TYPE: PRT
<213> ORGANISM: Homo sapiens

<400> SEQUENCE: 48

Arg Thr Ser Asn Leu Ala Ser
1               5

<210> SEQ ID NO 49
<211> LENGTH: 7
<212> TYPE: PRT
<213> ORGANISM: Homo sapiens

<400> SEQUENCE: 49

Trp Ala Ser Thr Arg Glu Ser
1               5

<210> SEQ ID NO 50
<211> LENGTH: 9
<212> TYPE: PRT
<213> ORGANISM: Homo sapiens

<400> SEQUENCE: 50

Phe Gln Gly Ser His Val Pro Leu Thr
1               5

<210> SEQ ID NO 51
<211> LENGTH: 9
<212> TYPE: PRT
<213> ORGANISM: Homo sapiens

<400> SEQUENCE: 51

Gln Gln Tyr His Ser Tyr Pro Tyr Thr
1               5

<210> SEQ ID NO 52
<211> LENGTH: 9
<212> TYPE: PRT
<213> ORGANISM: Homo sapiens

<400> SEQUENCE: 52

Ser Gln Ser Thr His Val Pro Trp Thr
1               5

<210> SEQ ID NO 53
<211> LENGTH: 9
<212> TYPE: PRT
<213> ORGANISM: Homo sapiens

<400> SEQUENCE: 53

Phe Gln Gly Ser His Val Pro Phe Thr
1               5

<210> SEQ ID NO 54
<211> LENGTH: 9
<212> TYPE: PRT
<213> ORGANISM: Homo sapiens

<400> SEQUENCE: 54

Gln Gln Phe His Ser Tyr Pro Tyr Thr
1               5

<210> SEQ ID NO 55
<211> LENGTH: 9
```

<212> TYPE: PRT
<213> ORGANISM: Homo sapiens

<400> SEQUENCE: 55

Gln Gln Tyr Tyr Ser Tyr Pro Tyr Thr
1               5

<210> SEQ ID NO 56
<211> LENGTH: 121
<212> TYPE: PRT
<213> ORGANISM: Homo sapiens

<400> SEQUENCE: 56

Glu Val Gln Leu Val Glu Thr Gly Gly Gly Leu Val Gln Pro Lys Gly
1               5                   10                  15

Ser Leu Lys Leu Ser Cys Ala Thr Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Thr Lys Ser Asn Asp Tyr Ala Thr Tyr Tyr Ala Asp
        50                  55                  60

Ser Val Lys Gly Arg Ile Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Val Gly Tyr Arg Pro Tyr Ala Met Asp Tyr Trp Gly
            100                 105                 110

Gln Gly Thr Ser Val Thr Val Ser Ser
        115                 120

<210> SEQ ID NO 57
<211> LENGTH: 121
<212> TYPE: PRT
<213> ORGANISM: Homo sapiens

<400> SEQUENCE: 57

Glu Val Gln Leu Val Glu Ser Gly Gly Asp Leu Val Lys Pro Gly Gly
1               5                   10                  15

Ser Leu Lys Phe Ser Cys Ala Ala Ser Gly Phe Thr Phe Ser Asn Tyr
                20                  25                  30

Ala Met Ser Trp Val Arg Gln Thr Pro Asp Lys Arg Leu Glu Trp Val
            35                  40                  45

Ala Thr Val Thr Ser Gly Gly Ser Tyr Thr Tyr Tyr Pro Asp Ser Val
        50                  55                  60

Arg Gly Arg Phe Thr Ile Ser Arg Asp Asn Ala Lys Asn Thr Leu Tyr
65                  70                  75                  80

Leu Gln Leu Ser Ser Leu Lys Ser Glu Asp Thr Ala Met Tyr Phe Cys
                85                  90                  95

Ala Arg Gln Asn Phe Gly Ser Arg Gly Trp Tyr Phe Asp Val Trp Gly
            100                 105                 110

Ala Gly Thr Thr Val Thr Val Ser Ser
        115                 120

<210> SEQ ID NO 58
<211> LENGTH: 120
<212> TYPE: PRT
<213> ORGANISM: Homo sapiens

<400> SEQUENCE: 58

```
Glu Val Met Leu Val Glu Ser Gly Gly Leu Val Lys Pro Gly Gly
 1               5                   10                  15

Ser Leu Lys Leu Ser Cys Ala Ala Ser Gly Phe Thr Phe Ser Ser Tyr
             20                  25                  30

Ala Met Ser Trp Val Arg Gln Thr Pro Glu Lys Arg Leu Glu Trp Val
             35                  40                  45

Ala Thr Ile Ser Asn Gly Gly Ser Tyr Thr Tyr Tyr Pro Asp Ser Val
             50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Met Tyr Tyr Cys
                 85                  90                  95

Ala Arg His Ser Asp Tyr Ser Gly Ala Trp Phe Ala Tyr Trp Gly Gln
            100                 105                 110

Gly Thr Leu Val Thr Val Ser Ala
            115                 120

<210> SEQ ID NO 59
<211> LENGTH: 120
<212> TYPE: PRT
<213> ORGANISM: Homo sapiens

<400> SEQUENCE: 59

Glu Val Gln Leu Gln Glu Ser Gly Pro Ser Leu Val Lys Pro Ser Gln
 1               5                   10                  15

Thr Leu Ser Leu Thr Cys Ser Val Thr Gly Asp Ser Phe Thr Ser Gly
             20                  25                  30

Tyr Trp Asn Trp Ile Arg Lys Phe Pro Gly Asn Lys Leu Glu Tyr Met
             35                  40                  45

Gly Tyr Ile Arg Tyr Ser Gly Asn Thr Tyr Tyr Asn Pro Ser Leu Lys
             50                  55                  60

Ser Arg Ile Ser Ile Thr Arg Asp Thr Ser Lys Asn Gln Tyr Tyr Leu
 65                  70                  75                  80

Gln Leu Ile Ser Val Thr Thr Glu Asp Thr Ala Thr Phe Tyr Cys Ala
                 85                  90                  95

Arg Ser Tyr Tyr Asp Tyr Asp Arg Ala Trp Phe Ala Tyr Trp Gly Gln
            100                 105                 110

Gly Ala Leu Val Thr Val Ser Ala
            115                 120

<210> SEQ ID NO 60
<211> LENGTH: 112
<212> TYPE: PRT
<213> ORGANISM: Homo sapiens

<400> SEQUENCE: 60

Asp Val Leu Met Thr Gln Thr Pro Leu Ser Leu Pro Val Ser Leu Gly
 1               5                   10                  15

Asp Gln Ala Ser Ile Ser Cys Arg Ser Ser Gln Asn Ile Val His Ser
             20                  25                  30

Asn Gly Asn Thr Tyr Leu Glu Trp Tyr Leu Gln Lys Pro Gly Gln Ser
             35                  40                  45

Pro Thr Leu Leu Ile Tyr Lys Val Ser Asn Arg Phe Ser Gly Val Pro
             50                  55                  60

Asp Arg Phe Ser Gly Ser Gly Ser Gly Thr Asp Phe Thr Leu Lys Ile
 65                  70                  75                  80
```

```
Ser Arg Val Glu Ala Glu Asp Leu Gly Val Tyr Tyr Cys Phe Gln Gly
            85                  90                  95

Ser His Val Pro Leu Thr Phe Gly Ala Gly Thr Lys Leu Glu Leu Lys
            100                 105                 110
```

<210> SEQ ID NO 61
<211> LENGTH: 112
<212> TYPE: PRT
<213> ORGANISM: Homo sapiens

<400> SEQUENCE: 61

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Asn Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
            85                  90                  95

Ser His Val Pro Leu Thr Phe Gly Ala Gly Thr Lys Leu Glu Leu Lys
            100                 105                 110
```

<210> SEQ ID NO 62
<211> LENGTH: 106
<212> TYPE: PRT
<213> ORGANISM: Homo sapiens

<400> SEQUENCE: 62

```
Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Met
            20                  25                  30

Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Tyr Thr
            85                  90                  95

Phe Gly Gly Gly Thr Lys Leu Glu Ile Lys
            100                 105
```

<210> SEQ ID NO 63
<211> LENGTH: 112
<212> TYPE: PRT
<213> ORGANISM: Homo sapiens

<400> SEQUENCE: 63

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30
```

```
Asn Gly Asn Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Trp Thr Phe Gly Gly Gly Thr Lys Leu Glu Ile Lys
                100                 105                 110
```

<210> SEQ ID NO 64
<211> LENGTH: 121
<212> TYPE: PRT
<213> ORGANISM: Homo sapiens

<400> SEQUENCE: 64

```
Glu Val Gln Leu Val Glu Thr Gly Gly Gly Leu Val Gln Pro Lys Gly
 1               5                  10                  15

Ser Leu Lys Leu Ser Cys Ala Thr Ser Gly Phe Thr Phe Asn Thr Tyr
                 20                  25                  30

Ala Met Asn Trp Val Arg Gln Ala Pro Gly Lys Gly Leu Glu Trp Val
             35                  40                  45

Ala Arg Ile Arg Thr Lys Ser Asn Asp Tyr Ala Thr Tyr Tyr Ala Asp
 50                  55                  60

Ser Val Lys Gly Arg Ile Thr Ile Ser Arg Asp Asp Ser Gln Ser Met
 65                  70                  75                  80

Leu Tyr Leu Gln Met Asn Asn Leu Lys Thr Glu Asp Thr Ala Met Tyr
                 85                  90                  95

Tyr Cys Val Arg Val Gly Tyr Arg Pro Tyr Ala Met Asp Tyr Trp Gly
                100                 105                 110

Gln Gly Thr Ser Val Thr Val Ser Ser
            115                 120
```

<210> SEQ ID NO 65
<211> LENGTH: 121
<212> TYPE: PRT
<213> ORGANISM: Homo sapiens

<400> SEQUENCE: 65

```
Glu Val Gln Leu Val Glu Ser Gly Gly Asp Leu Val Lys Pro Gly Gly
 1               5                  10                  15

Ser Leu Lys Phe Ser Cys Ala Ala Ser Gly Phe Thr Phe Ser Asn Tyr
                 20                  25                  30

Ala Met Ser Trp Val Arg Gln Thr Pro Asp Lys Arg Leu Glu Trp Val
             35                  40                  45

Ala Thr Val Thr Ser Gly Gly Ser Tyr Thr Tyr Tyr Pro Asp Ser Val
 50                  55                  60

Arg Gly Arg Phe Thr Ile Ser Arg Asp Asn Ala Lys Asn Thr Leu Tyr
 65                  70                  75                  80

Leu Gln Leu Ser Ser Leu Lys Ser Glu Asp Thr Ala Met Tyr Phe Cys
                 85                  90                  95

Ala Arg Gln Asn Phe Gly Ser Arg Gly Trp Tyr Phe Asp Val Trp Gly
                100                 105                 110

Ala Gly Thr Thr Val Thr Val Ser Ser
            115                 120
```

<210> SEQ ID NO 66
<211> LENGTH: 120
<212> TYPE: PRT
<213> ORGANISM: Homo sapiens

<400> SEQUENCE: 66

```
Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Asn Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg His Ser Asp Tyr Ser Gly Ala Trp Phe Ala Tyr Trp Gly Gln
            100                 105                 110

Gly Thr Leu Val Thr Val Ser Ala
        115                 120
```

<210> SEQ ID NO 67
<211> LENGTH: 120
<212> TYPE: PRT
<213> ORGANISM: Homo sapiens

<400> SEQUENCE: 67

```
Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Phe Thr Ser Gly
            20                  25                  30

Tyr Trp Asn Trp Ile Arg Lys Phe Pro Gly Asn Lys Leu Glu Tyr Met
        35                  40                  45

Gly Tyr Ile Arg Tyr Ser Gly Asn Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Ile Ser Val Thr Thr Glu Asp Thr Ala Thr Phe Tyr Cys Ala
                85                  90                  95

Arg Ser Tyr Tyr Asp Tyr Asp Arg Ala Trp Phe Ala Tyr Trp Gly Gln
            100                 105                 110

Gly Ala Leu Val Thr Val Ser Ala
        115                 120
```

<210> SEQ ID NO 68
<211> LENGTH: 118
<212> TYPE: PRT
<213> ORGANISM: Homo sapiens

<400> SEQUENCE: 68

```
Gln Val Gln Leu Lys Gln Ser Gly Pro Ser Leu Val Gln Pro Ser Gln
1               5                   10                  15

Ser Leu Ser Ile Thr Cys Ser Val Ser Gly Phe Ser Leu Thr Ser Tyr
            20                  25                  30

Gly Val His Trp Val Arg Leu Ser Pro Gly Lys Gly Leu Glu Trp Leu
```

35                  40                  45
Gly Val Ile Trp Arg Gly Gly Ser Thr Asp Tyr Ser Ala Ala Phe Met
         50                  55                  60

Ser Arg Leu Ser Ile Thr Lys Asp Asn Ser Lys Ser Gln Val Phe Phe
 65                  70                  75                  80

Lys Met Ser Ser Leu Gln Ala Asp Asp Thr Ala Ile Tyr Tyr Cys Ala
                 85                  90                  95

Lys Leu Leu Arg Ser Val Gly Gly Phe Ala Asp Trp Gly Gln Gly Thr
                100                 105                 110

Leu Val Thr Val Ser Ala
            115

<210> SEQ ID NO 69
<211> LENGTH: 120
<212> TYPE: PRT
<213> ORGANISM: Homo sapiens

<400> SEQUENCE: 69

Glu Val Met Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Asn Tyr
                 20                  25                  30

Ala Met Ser Trp Val Arg Gln Thr Pro Glu Lys Arg Leu Glu Trp Val
             35                  40                  45

Ala Thr Ile Ser Thr Gly Gly Ser Tyr Thr Tyr Tyr Pro Asp Ser Val
         50                  55                  60

Lys Gly Arg Phe Thr Ile Ser Arg Asp Asn Ala Asn Asn Ala Leu Tyr
 65                  70                  75                  80

Leu Gln Met Ser Ser Leu Arg Ser Glu Asp Thr Ala Met Tyr Tyr Cys
                 85                  90                  95

Ala Arg His Ser Asp Tyr Ser Gly Ala Trp Phe Ala Tyr Trp Gly Arg
                100                 105                 110

Gly Thr Leu Val Thr Val Ser Ala
            115                 120

<210> SEQ ID NO 70
<211> LENGTH: 120
<212> TYPE: PRT
<213> ORGANISM: Homo sapiens

<400> SEQUENCE: 70

Glu Val Gln Leu Gln Glu Ser Gly Pro Ser Leu Val Lys Pro Ser Gln
 1               5                  10                  15

Thr Leu Ser Leu Thr Cys Ser Val Thr Gly Asp Ser Phe Thr Ser Gly
                 20                  25                  30

Tyr Trp Asn Trp Ile Arg Lys Phe Pro Gly Asn Lys Leu Glu Tyr Met
             35                  40                  45

Gly Tyr Ile Arg Tyr Ser Gly Asn Thr Tyr Tyr Asn Pro Ser Leu Lys
         50                  55                  60

Ser Arg Ile Ser Ile Thr Arg Asp Thr Ser Lys Asn Gln Tyr Tyr Leu
 65                  70                  75                  80

Gln Leu Ile Ser Val Thr Thr Glu Asp Thr Ala Thr Phe Tyr Cys Ala
                 85                  90                  95

Arg Ser Tyr Tyr Asp Tyr Asp Arg Ala Trp Phe Ala Tyr Trp Gly Gln
                100                 105                 110

Gly Ala Leu Val Thr Val Ser Ala

<210> SEQ ID NO 71
<211> LENGTH: 120
<212> TYPE: PRT
<213> ORGANISM: Homo sapiens

<400> SEQUENCE: 71

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Asp Tyr Gly Asn Tyr Ala Met Asp Tyr Trp Gly Gln
            100                 105                 110

Gly Thr Ser Val Thr Val Ser Ser
        115                 120

<210> SEQ ID NO 72
<211> LENGTH: 112
<212> TYPE: PRT
<213> ORGANISM: Homo sapiens

<400> SEQUENCE: 72

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Thr Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 73
<211> LENGTH: 112
<212> TYPE: PRT
<213> ORGANISM: Homo sapiens

<400> SEQUENCE: 73

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Asn Ser
            20                  25                  30

Asn Gly Asn Thr Tyr Leu Glu Trp Tyr Leu Gln Lys Pro Gly Gln Ser
        35                  40                  45

```
Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Thr Leu Glu Leu Lys
            100                 105                 110
```

<210> SEQ ID NO 74
<211> LENGTH: 106
<212> TYPE: PRT
<213> ORGANISM: Homo sapiens

<400> SEQUENCE: 74

```
Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Val Ser Tyr Met Tyr
                20                  25                  30

Trp Tyr Gln Gln Lys Pro Gly Ser Ser Pro Lys Pro Trp Ile Tyr
            35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Tyr Thr
                85                  90                  95

Phe Gly Gly Gly Thr Lys Leu Glu Ile Lys
            100                 105
```

<210> SEQ ID NO 75
<211> LENGTH: 112
<212> TYPE: PRT
<213> ORGANISM: Homo sapiens

<400> SEQUENCE: 75

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110
```

<210> SEQ ID NO 76
<211> LENGTH: 112
<212> TYPE: PRT
<213> ORGANISM: Homo sapiens

<400> SEQUENCE: 76

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Asn
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Tyr Cys Phe Gln Gly
            85                  90                  95

Ser His Val Pro Phe Thr Phe Gly Ser Gly Thr Lys Leu Glu Ile Lys
            100                 105                 110
```

<210> SEQ ID NO 77
<211> LENGTH: 106
<212> TYPE: PRT
<213> ORGANISM: Homo sapiens

<400> SEQUENCE: 77

```
Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Val Ser Tyr Met Tyr
            20                  25                  30

Trp Tyr Gln Gln Lys Pro Gly Ser Ser Pro Lys Pro Trp Ile Tyr
    35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65              70                  75                  80

Asp Ala Ala Thr Tyr Tyr Cys Gln Gln Phe His Ser Tyr Pro Tyr Thr
            85                  90                  95

Phe Gly Gly Gly Thr Lys Leu Glu Ile Lys
            100                 105
```

<210> SEQ ID NO 78
<211> LENGTH: 112
<212> TYPE: PRT
<213> ORGANISM: Homo sapiens

<400> SEQUENCE: 78

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Phe Cys Ser Gln Ser
            85                  90                  95

Thr His Val Pro Trp Thr Phe Gly Gly Gly Thr Lys Leu Glu Ile Lys
            100                 105                 110
```

```
<210> SEQ ID NO 79
<211> LENGTH: 113
<212> TYPE: PRT
<213> ORGANISM: Homo sapiens

<400> SEQUENCE: 79

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys

<210> SEQ ID NO 80
<211> LENGTH: 140
<212> TYPE: PRT
<213> ORGANISM: Homo sapiens

<400> SEQUENCE: 80

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
        50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
            130                 135                 140
```